(12) United States Patent
Nadkarmi et al.

(10) Patent No.: US 10,191,031 B2
(45) Date of Patent: Jan. 29, 2019

(54) SYSTEM AND METHODS ESTIMATION OF MECHANICAL PROPERTIES AND SIZE OF LIGHT-SCATTERING PARTICLES IN MATERIALS

(71) Applicant: THE GENERAL HOSPITAL CORPORATION, Boston, MA (US)

(72) Inventors: Seemantinin K. Nadkarmi, Cambridge, MA (US); Zelnab Hajjarian, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 66 days.

(21) Appl. No.: 15/114,868

(22) PCT Filed: Feb. 2, 2015

(86) PCT No.: PCT/US2015/014066
§ 371 (c)(1),
(2) Date: Jul. 28, 2016

(87) PCT Pub. No.: WO2015/160418
PCT Pub. Date: Oct. 22, 2015

(65) Prior Publication Data
US 2017/0003271 A1 Jan. 5, 2017

Related U.S. Application Data
(60) Provisional application No. 61/934,433, filed on Jan. 31, 2014.

(51) Int. Cl.
*G01N 33/49* (2006.01)
*G01N 11/00* (2006.01)
(Continued)

(52) U.S. Cl.
CPC ......... *G01N 33/4905* (2013.01); *G01N 11/00* (2013.01); *G01N 15/0211* (2013.01);
(Continued)

(58) Field of Classification Search
CPC ........... G01N 33/4905; G01N 15/0211; G01N 2015/0065; G01N 21/21; G01N 11/00;
(Continued)

(56) References Cited

U.S. PATENT DOCUMENTS

| 3,180,210 A | 4/1965 | Tyler |
| 4,134,679 A * | 1/1979 | Wertheimer ....... G01N 15/0205 250/574 |
| 5,818,583 A | 10/1998 | Sevick-Muraca et al. |
| 6,397,099 B1 | 5/2002 | Chance |
| 6,958,816 B1 | 10/2005 | Dagariu et al. |
| 2007/0171419 A1 | 7/2007 | Shribak et al. |

(Continued)

OTHER PUBLICATIONS

International Search Report and Written Opinion dated Oct. 7, 2015 in connection with PCT/US2015/014066.

*Primary Examiner* — Christopher Adam Hixson
(74) *Attorney, Agent, or Firm* — Quarles & Brady LLP

(57) ABSTRACT

System and method for determining a viscoelastic modulus of a sample with the use of optical data and an average size of light-scattering particles, of such sample, that has been derived from the optical data in reliance of angular dependence of a radiant flux profile determined from laser speckles formed by the sample and, in required, on a refractive index mismatch between light-scattering particles and sample medium hosting such particles. The determination is optionally carried out by taking into account at least one of absorption coefficient and reduced scattering coefficient of the sample, which are also determined from the same optical data. Laser speckle may be formed for different combinations of polarization states of sample-illuminating light and detected light and/or different wavelengths to account for polydisperse nature of the sample.

34 Claims, 18 Drawing Sheets

(51) Int. Cl.
  *G01N 21/21*   (2006.01)
  *G01N 15/02*   (2006.01)
  *G01N 21/51*   (2006.01)
  *G01N 15/00*   (2006.01)
  *G01N 21/47*   (2006.01)

(52) U.S. Cl.
  CPC ............. *G01N 21/21* (2013.01); *G01N 21/51* (2013.01); *G01N 2015/0065* (2013.01); *G01N 2015/0294* (2013.01); *G01N 2021/4792* (2013.01); *G01N 2201/061* (2013.01); *G01N 2201/0683* (2013.01); *G01N 2201/12* (2013.01); *G01N 2203/0094* (2013.01)

(58) Field of Classification Search
  CPC ..... G01N 2011/008; G01N 2011/0026; G01N 2201/0683; G01N 2021/4792; G01N 2203/0094
  See application file for complete search history.

(56) References Cited

U.S. PATENT DOCUMENTS

| | | |
|---|---|---|
| 2008/0220512 A1 | 9/2008 | Koh et al. |
| 2010/0062545 A1 | 3/2010 | Geddes |
| 2012/0062891 A1 | 3/2012 | Brunel |
| 2012/0130253 A1 | 5/2012 | Nadkarni et al. |
| 2012/0301967 A1 | 11/2012 | Nadkarni |

\* cited by examiner

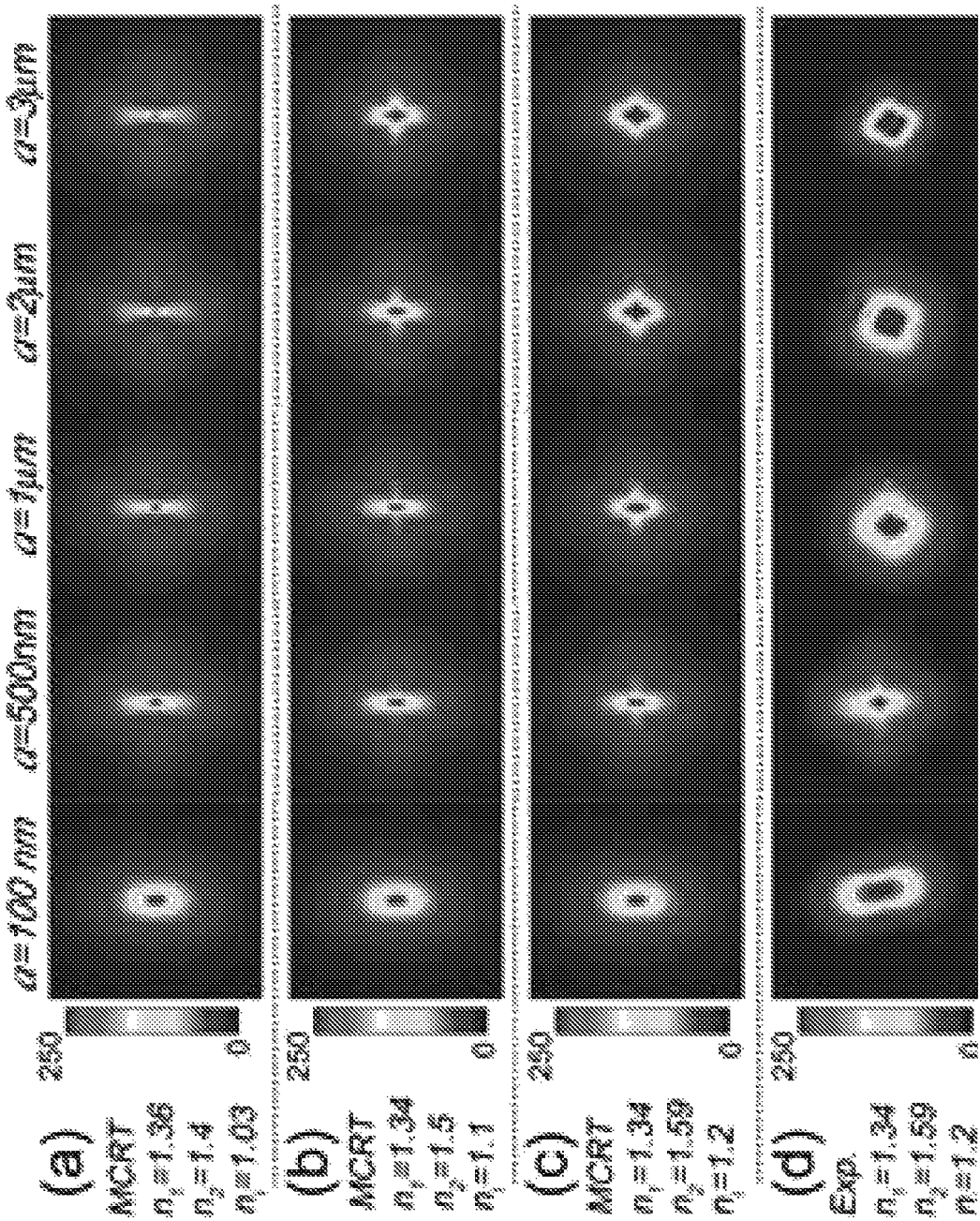

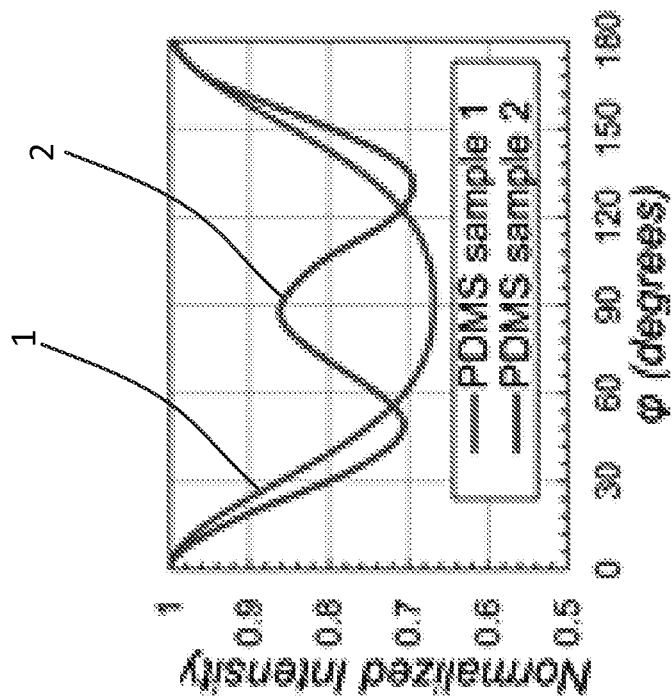
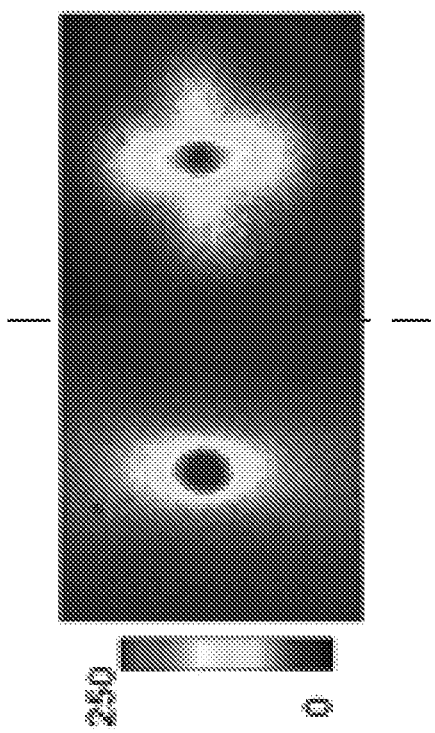
FIG. 4A  FIG. 4B  FIG. 4C

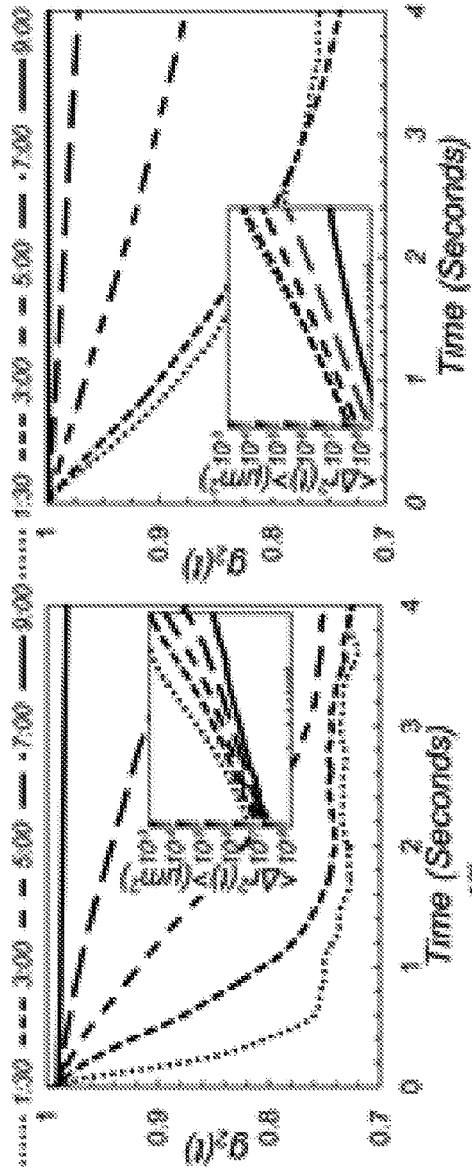
FIG. 4E
FIG. 4D
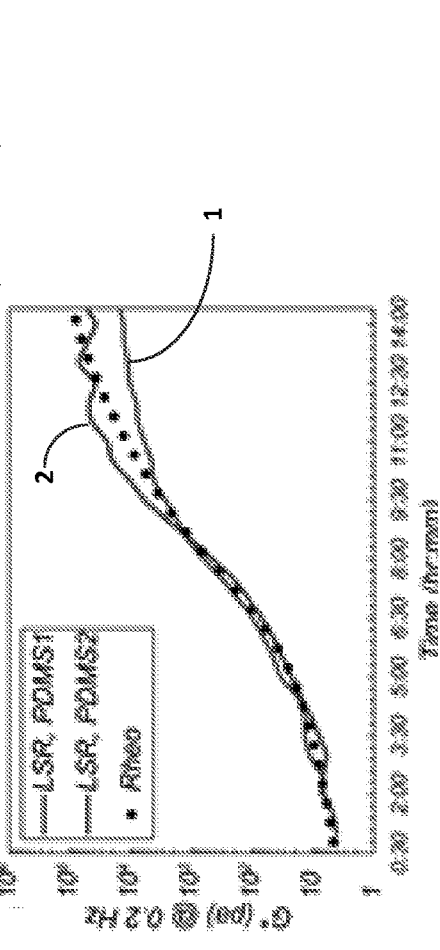
FIG. 4F

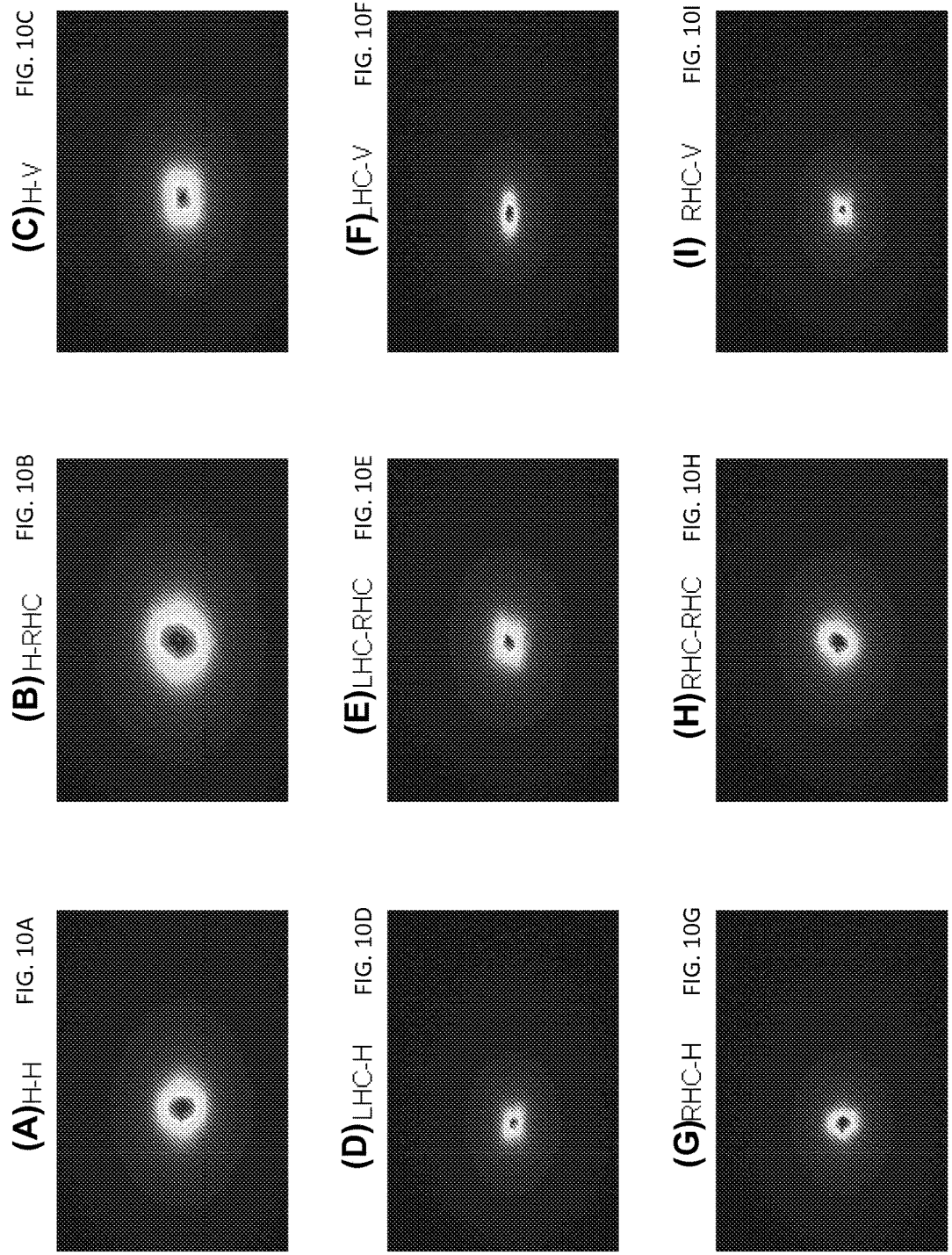

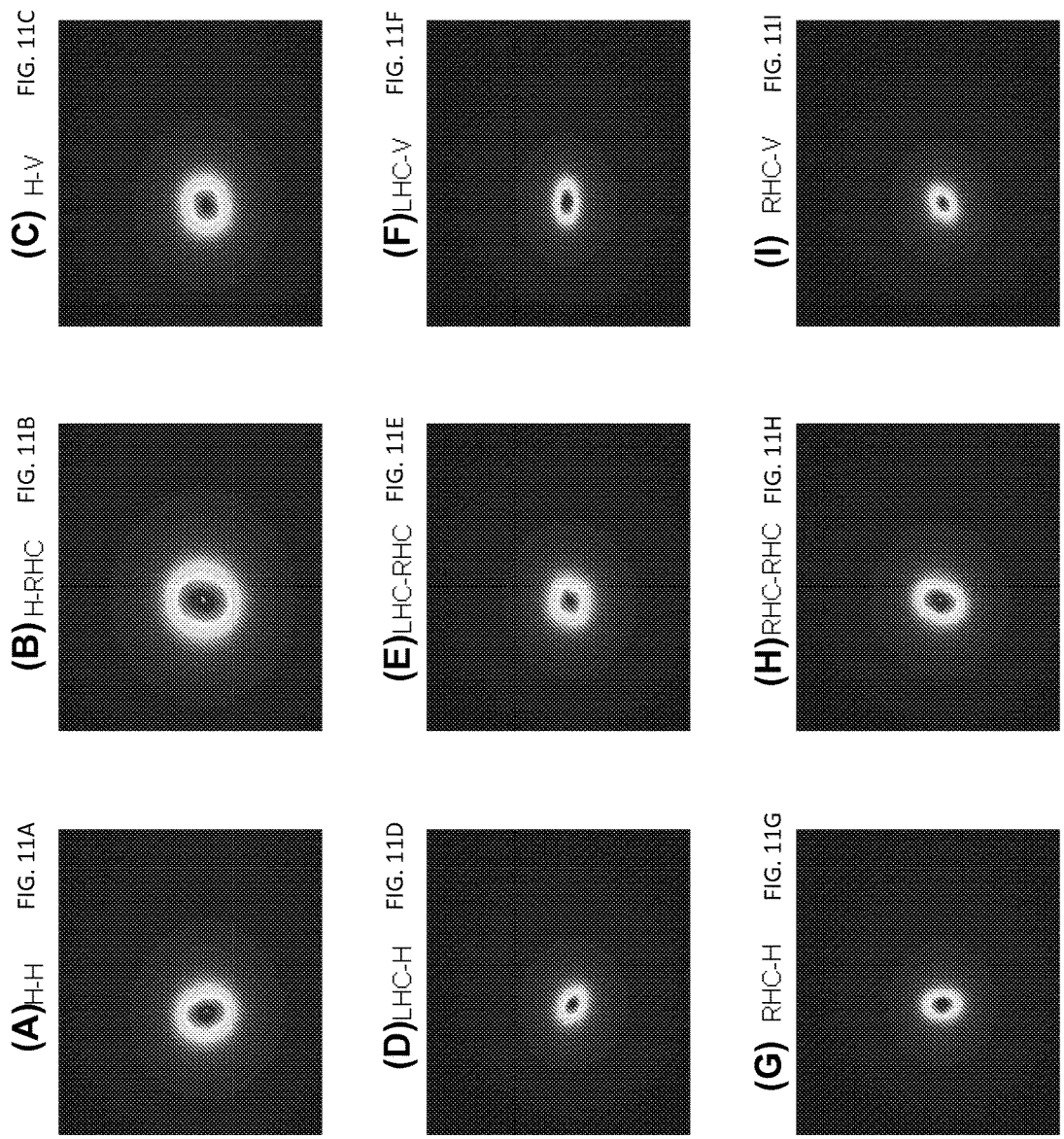

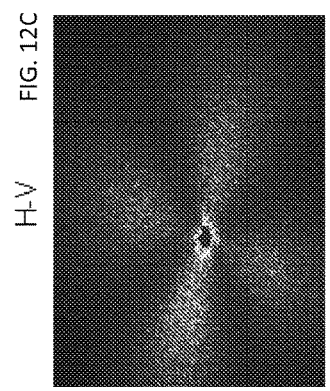
FIG. 12C H-V
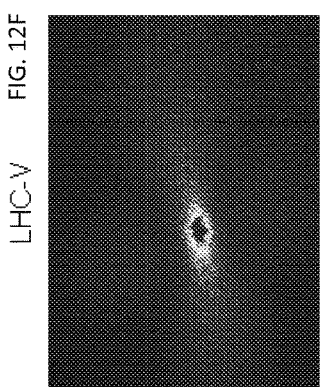
FIG. 12F LHC-V
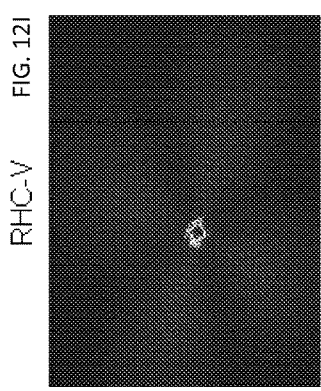
FIG. 12I RHC-V
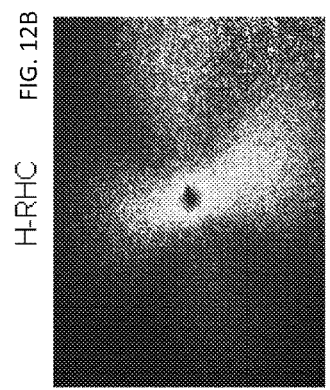
FIG. 12B H-RHC
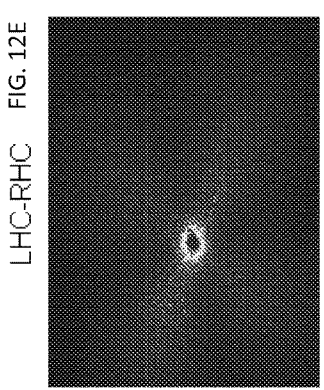
FIG. 12E LHC-RHC
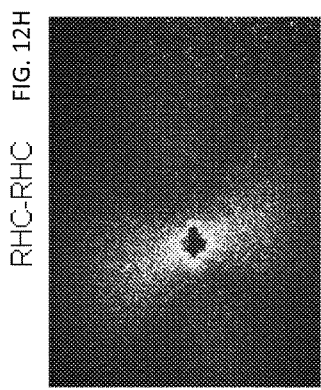
FIG. 12H RHC-RHC
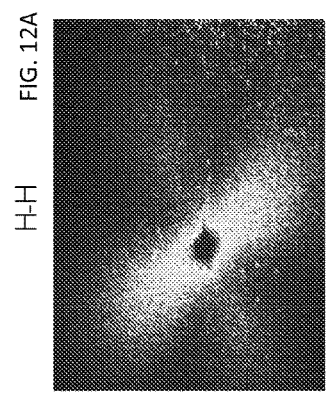
FIG. 12A H-H
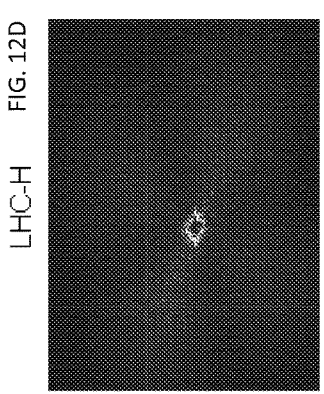
FIG. 12D LHC-H
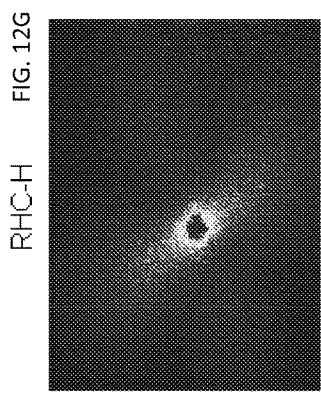
FIG. 12G RHC-H

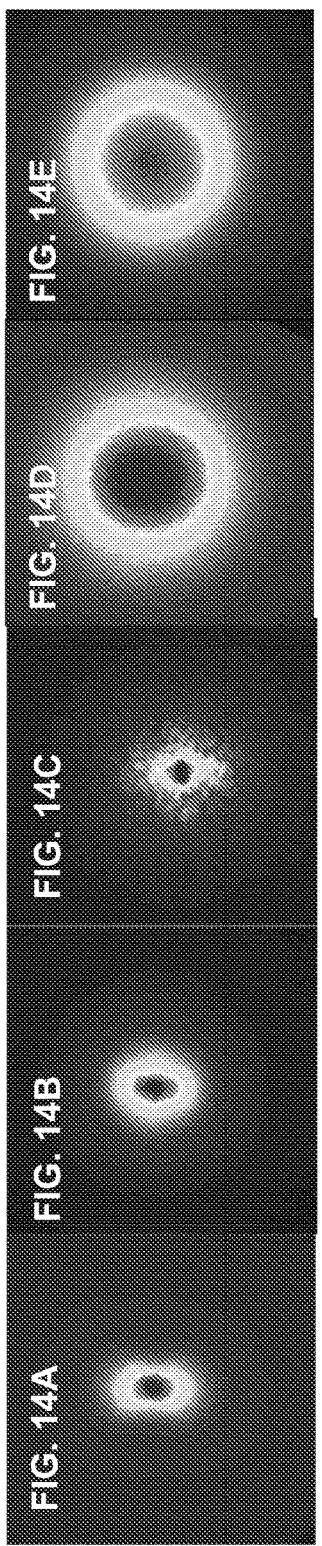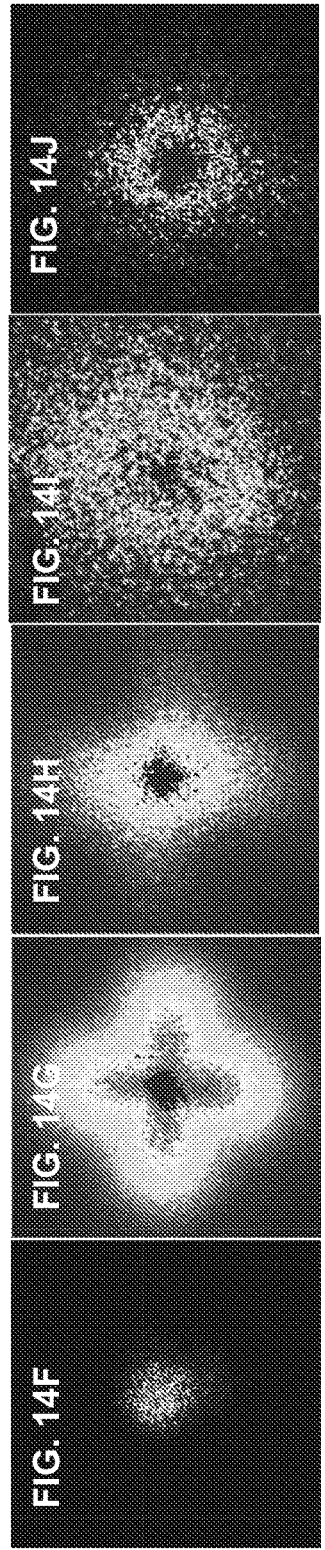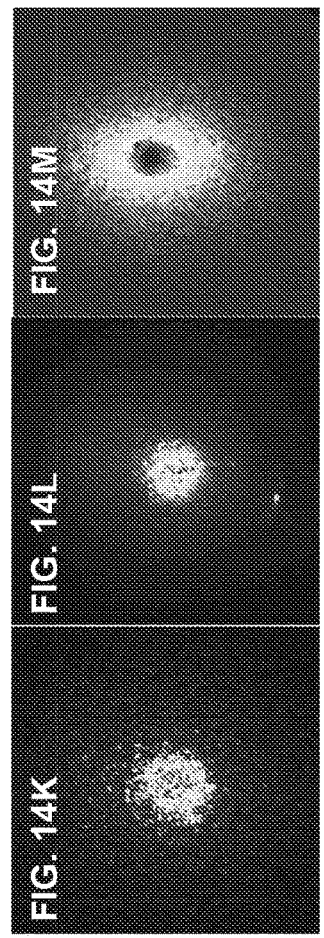

SYSTEM AND METHODS ESTIMATION OF MECHANICAL PROPERTIES AND SIZE OF LIGHT-SCATTERING PARTICLES IN MATERIALS

This application is a 371 application of PCT/US2015/014066 filed Feb. 2, 2015, which claims priority from and benefit of the U.S. Provisional Patent Application Ser. No. 61/934,433 filed on Jan. 31, 2014. The disclosures of which are incorporated by reference herein for all purposes.

STATEMENT REGARDING FEDERALLY SPONSORED RESEARCH

This invention was made with government support under grant number HL119867 awarded by the National Institutes of Health. The government has certain rights in this invention.

TECHNICAL FIELD

The present invention relates to optical systems and methods for the measurement and monitoring of the material properties of samples including biological fluids and, in particular, to a means for determining viscoelastic modulus of a sample with the use of a size of light-scattering particles determined based on analysis of electromagnetic radiation that has interacted with the sample during such monitoring.

BACKGROUND ART

Laser Speckle Rheology (LSR) is an optical methodology for assessing the viscoelastic properties of materials with several industrial, biological, and medical applications. The quantification of the viscoelastic modulus, $G^*(\omega)$, of a material in LSR may be effectuated, for example, by analyzing the temporal fluctuations of speckle patterns. While the size of scattering particles within the material also influences the rate of speckle fluctuations (independently from the contributions of the mechanical properties of the sample on such rate), the estimation of the viscoelastic properties made to date in related art was neglecting this factor, which in some cases could potentially lead to inaccurate estimates of $G^*(\omega)$ and erroneous characterization of materials (for example, erroneous characterization of viscoelastic properties in biological fluids, such as blood and its components, the knowledge of which is rather critical in biological and medical applications, or in industrial polymers, substance or fluids, food or dairy products). There remains a need, therefore, to account for the influence of particle size on the characterization of materials with LSR.

SUMMARY

An embodiment of the present invention provides a system for use in determining a viscoelastic modulus of a sample. The system includes a source of electromagnetic radiation (such as an optical light source or a laser, for example); an optical data acquisition system having an optical detector configured to receive electromagnetic radiation that was produced by the source and has interacted with the sample, and to acquire optical data representing scattering of said electromagnetic radiation by multiple light-scattering of the sample; and a processor operably cooperated with the optical data acquisition system and programmed a) to determine a size of said light-scattering particles based on a radiant flux profile associated with the irradiated sample and derived from the optical data; and b) to calculate a mean square displacement (MSD) value based on intensity temporal autocorrelation data, the intensity temporal autocorrelation data having been determined based on the optical data. The processor may be further programmed to determine, from the acquired optical data, an angle-dependent pattern of the radiant flux profile; and to determine an average size of the light-scattering particles of the sample by comparing a first value with a map of second values. The first value characterizes a distribution of light irradiance in the radiant flux profile. The map of second values contains distributions of light irradiance across reference radiant flux profiles that have been calculated as functions of (j) a first variable representing average sizes of light-scattering particles, (jj) a second variable representing refractive index mismatch between the light-scattering particles and a medium containing said particles, and, optionally, (jjj) a third variable representing a wavelength of the electromagnetic radiation.

An embodiment of the invention also provides a method for determining a viscoelastic modulus of a sample with the use of an optical system. The method includes the steps of a step of acquisition, with an optical detector, of optical data representing time evolution of a speckle associated with light-scattering particles of the sample irradiated with light from a light source through the illumination system. The method includes a step of determining a size of the light-scattering particles based on radiant flux profile derived from acquired optical data. The method further includes a step of calculating, with a programmable processor, a mean square displacement (MSD) value based on intensity temporal autocorrelation data, the intensity temporal autocorrelation data having been determined based on time-varying intensity fluctuations of the acquired optical data. Both the determination of the light-scattering particle size and the determination of the viscoelastic modulus are performed with the use of the same illumination system and based on the same acquired optical data.

BRIEF DESCRIPTION OF THE DRAWINGS

The invention will be more fully understood by referring to the following Detailed Description in conjunction with the generally not-to scale Drawings, of which:

FIGS. 2A, 2B, and 2C each illustrates theoretically calculated, with the use of the MCRT algorithm) radiant flux profiles (interchangeably referred to as diffuse remittance profiles, or diffuse reflection profiles, DRPs) for samples containing light scattering particles with radius values, a, of 0.1, 0.5, 1, 2, and 3 μm, and $n_i$ values of 1.03 (FIG. 2A), 1.1 (FIG. 2B), and 1.2 (FIG. 2C). The vector of polarization of light incident on the material is parallel to samples' surfaces.

FIG. 2D shows experimentally procured DRPs for samples with the same scattering particle sizes as those of FIGS. 2A, 2B, 2C and $n_i$=1.2 (for comparison with those of FIG. 2C). The side bar represents the pixel irradiance level (0-255).

FIGS. 4A, 4B present experimentally evaluated (with transmission axes of the polarizers 114, 130 of FIG. 1) DRPs for polydimethylsiloxane samples. The side bar represents the pixel irradiance level.

FIG. 4C shows dependences of normalized irradiance values vs. angle, derived from the DRPs of FIGS. 4A, 4B. The values of corresponding ratios of normalized irradiance $\hat{I}$ are 0.67 and 0.87, respectively, corresponding to $a_1$~0.25 µm and $a_2$~0.75 µm (derived from comparison with the calibration map of FIG. 2F).

FIGS. 4D, 4E illustrate the g2(t) curves for PDMS1 and PDMS2 that are distinct due to differences in particle size, despite identical G* values.

FIG. 4F shows the evolution of G* (at 0.2 Hz) measured using the optical methodology of the present invention (lines) and with mechanical rheometry (dots).

FIGS. 10A through 10I depict DRPs for Half & Half, experimentally determined with polarizer 114 and analyzer 130 of FIG. 1 configured for the following status of polarization of light: FIG. 10A: Horizontal-Horizontal (H-H); FIG. 10B: Horizontal-Right Hand Circular (H-RHC); FIG. 10C: Horizontal-Vertical (H-V); transmission axes are perpendicular to one another); FIG. 10D: Left Hand Circular-Horizontal (LHC-H); FIG. 10E: Left Hand Circular-Right Hand Circular (LHC-RHC) (transmission axes are perpendicular to one another); FIG. 10F: Left Hand Circular-vertical (LHC-V); FIG. 10G: Right Hand Circular-Horizontal (RHC-H); FIG. 10H: Right Hand Circular-Right Hand Circular (RHC-RHC) (transmission axes are parallel to one another); FIG. 10I: Right Hand Circular-Vertical (RHC-V);

FIGS. 11A through 11I depict DRPs for Intralipid, experimentally determined with polarizer 114 and analyzer 130 of FIG. 1 configured for the following status of polarization of light: FIG. 11A: H-H; FIG. 11B: H-RHC; FIG. 11C: H-V (transmission axes are perpendicular to one another); FIG. 11D: LHC-H; FIG. 11E: LHC-RHC (transmission axes are perpendicular to one another); FIG. 11F: LHC-V; FIG. 11G: RHC-H; FIG. 11H: RHC-RHC (transmission axes are parallel to one another); FIG. 11I: RHC-V.

FIG. 12A through 12I depict DRPs for Blood, experimentally determined with polarizer 114 and analyzer 130 of FIG. 1 configured for the following status of polarization of light: FIG. 12A: H-H; FIG. 12B: H-RHC; FIG. 12C: H-V (transmission axes are perpendicular to one another); FIG. 12D: LHC-H; FIG. 12E: LHC-RHC (transmission axes are perpendicular to one another); FIG. 12F: LHC-V; FIG. 12G: RHC-H; FIG. 12H: RHC-RHC (transmission axes are parallel to one another); FIG. 12I: RHC-V;

FIGS. 14A, 14B, 14C, 14D, 14E, 14F, 14G, 4H, 14I, 14J, 14K, 14L, 14M illustrate DBRs experimentally determined for Intra-lipid, Half & Half, Butter, Synovial Fluid, Vitreous Humorous, Bile, Blood, Plasma, Cartilage, Calcific Plaque, Fibrous Plaque, and Lipid-rich Plaque with the set-up of FIG. 1, in which transmission axes of polarizer 114 and analyzer 130 are parallel to one another;

Figure 1:
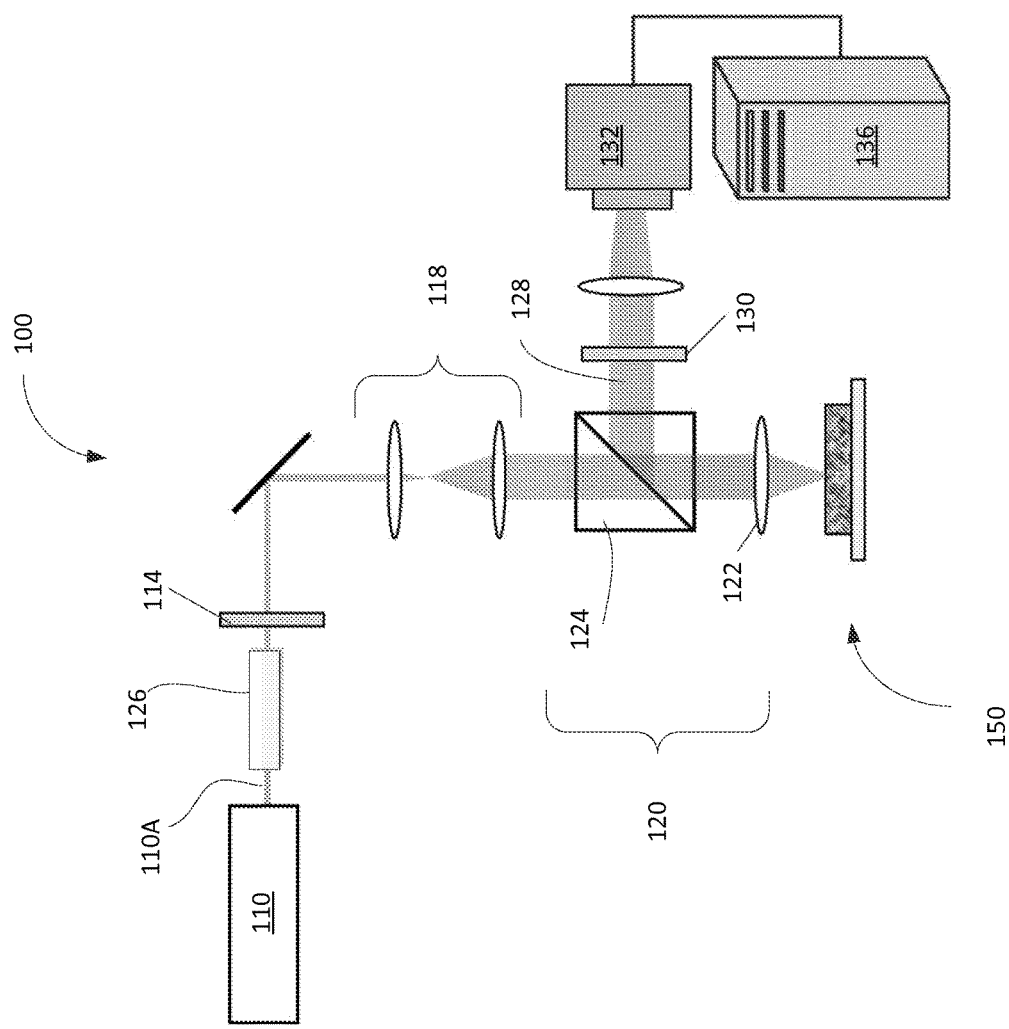
FIG. 1 is an embodiment of a system shown to operate in a backscattering regime and configured for measurements of irradiance of light that has interacted with a chosen material (such as, for example, a biological sample: blood, individual blood constituents, urine)

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

In accordance with preferred embodiments of the present invention, methods and apparatus are disclosed for the determination of a viscoelastic modulus of a material based on light distribution received from the material, that includes an optical determination of the average size of light-scattering particles (scatterers of light that are inherent to the material being measured) based on the same light distribution. In particular, the determination of such average particle size is rooted in optical measurement of the azimuth-angle dependence of the diffuse reflectance profile (remitted irradiance profile, radiant flux profile), including time-averaged speckle intensities obtained by illuminating the sample and detecting (whether in reflection or transmission through the sample) light that interacted with the sample in linear (horizontal/vertical) and/or elliptical (for example, right hand and left hand circular) polarization states of light, thereby permitting the accurate quantification of the viscoelastic moduli even in materials with an a priori unknown particle size.

The ability to evaluate viscoelastic properties of materials is useful in many applications, for example in polymer engineering, food sciences, and biomedical imaging. The viscoelastic behavior of a material is usually described by the viscoelastic modulus, $G^*(\omega)$, and is often measured by a mechanical rheometer, in which a specimen is sheared between two parallel plates in an oscillatory manner and the ratio of the exerted stress to the resulting strain is calculated.

Prior studies have demonstrated that LSR can also be used for quantification of $G^*(\omega)$ in an optical, non-contact manner, using small sample volumes. In compliant materials, the unrestricted Brownian excursions of light scatters (interchangeably referred to herein as scattering particles) elicit a rapidly fluctuating speckle pattern, whereas in rigid substrates the restrained particle displacements induce limited speckle modulation. Cross-correlation analysis of the speckle frame series returns the speckle irradiance autocorrelation curve, $g_2(t)$, from which the mean square displacement (MSD) of Brownian particles, $\langle \Delta r^2(t) \rangle$, is deduced. The generalized Stokes-Einstein relation (GSER) can then be used to extract the $G^*(\omega)$:

$$G^*(\omega) = \frac{K_B T}{\pi a \langle \Delta r^2(1/\omega) \rangle \Gamma(1 + \alpha(1/\omega))} \quad (1)$$

In Eq. (1), $K_B$ is the Boltzman constant ($1.38 \times 10^{23}$), T is the temperature (in Kelvins), a is the average sphere-equivalent radius of scattering particles, $\alpha$ is the log-log slope of MSD at the loading frequency $\omega=1/t$, $\Gamma$ is the gamma function, and $a(t) = \partial \log \langle \Delta r^2(t) \rangle / \partial \log(t)$ corresponds to the logarithmic derivative of MSD. The accurate quantification of $G^*(\omega)$ from the $g_2(t)$ curve is complicated, because speckle fluctuations are modulated and/or modified not only by the viscoelastic compliance of the material, but also by optical properties and scattering particle size distribution of the material of the sample at hand.

The inventors have already identified the contribution of optical properties of the material on the viscoelastic modulus, by showing that the $g_2(t)$ curve is related to both the particles' MSD and the optical absorption and reduced scattering coefficients of the material, $\mu_a$ and $\mu_s'$ (see, for example, Z. Hajjarian et al., *Opt. Express*, 22, 6349-6361, 2014; see also PCT/US2013/059906, published as WO 2014/043609), and also showed that temporal averaging of speckle frames is one method to yield the diffuse remittance profile (DRP, interchangeably referred to herein as a radiant flux profile or remitted irradiance profile) of the sample from which $\mu_a$ and $\mu_s'$ are derived. Given these coefficients, MSD is seamlessly deduced from $g_2(t)$ with knowledge of optical parameters of the sample. The above-identified patent application and other previously-filed patent documents identified in this disclosure, each of which is incorporated herein by reference, are referred to as Our Prior Applications.

Apart from optical properties, the size of Brownian scattering particles also modifies the speckle fluctuations, confounding the accurate estimation of $G^*(\omega)$. Equation (1) clarifies that for a medium or material of given $G^*(\omega)$, the MSD is adjusted by the scattering particle size such that for smaller particles MSD grows faster and accelerates speckle autocorrelation. Therefore, to derive $G^*(\omega)$ from MSD, the scattering particle size needs to be estimated. While other optical techniques such as dynamic light scattering (DLS) and angle-resolved low coherence interferometry (a/LCI) have been independently employed previously for particle sizing applications (see, for example, Wax et al., *J. Opt. Soc. Am. A*, 19, 737-744, 2002), such methodologies have practical constraints. In particular, the limitation of DLS to dilute samples and complexity of a/LCI hardware restricts their integration into the LSR system to characterize turbid materials. Neither of these techniques was even considered in connection with the process of determination of the viscoelastic modulus of the medium. Moreover, when the LSR-based experiments are already in progress to determine the viscoelastic modulus, the determination of light-scatterer size with the use of experimentally different methodologies of the DLS and a/LCI requires, at a minimum, a significant complication of and interruption/delay in the experimental process of defining the viscoelastic modulus of the medium.

The idea of the present invention stems from the unexpected realization that the average dimension, a, of the light-scattering particles already intrinsically present in the medium under the optical testing (such as, for example, the LSR-based investigation), can be determined from the diffuse remittance profile data (such as, for example, speckle data) acquired during the optical testing itself and does not require a measurement that is auxiliary, independent, unrelated to the immediate optical testing process. Accordingly, the system and methodology configured according to the idea of the present invention become integral, self-sufficient and self-contained for the purposes of the characterization of the viscoelastic properties of the chosen medium. The examples of embodiments discussed below correspond to the use of the same laser source and the same optical system to obtain time-averaged laser speckle patterns to calculate the DRP and also measure time-resolved speckle intensity fluctuations. In related embodiments, an additional light source such as a broad band light source, arc lamp or white light source or others could be used to illuminate the sample, in which case the DRP and intensity fluctuations are determined from patterns of light diffused by the sample.

It was unexpectedly discovered that measurement of the DRPs, derived from time-averaged speckle frames, exhibits certain azimuth angle dependence, that depends both on the average scattering size, a, and the refractive index mismatch between the materials of light-scattering particles and the medium hosting these particles (one example of presenting such index mismatch may be a ratio of corresponding indices, as discussed below). In other words, it was empirically discovered that DRPs change their shapes in a repeatable but a priori not predictable manner as a function of the particle size and the value of index mismatch. Practical implementations of the invention, as discussed below, demonstrate that changes in the DRP shape (caused by varying a and/or $n_i$) may serve as the basis for the optical estimation of the light-scattering particle size (at one or multiple polarization states and/or wavelengths) and the determination of the $G^*(\omega)$ from the same optical data and without interrupting or complicating the LSR-based measurement of the $G^*(\omega)$, thereby improving the precision and accuracy of determination of $G^*(\omega)$ during the LSR procedure itself, and in contradistinction with methodologies utilized to date.

Experimental Verification of the DRP Patterns and Comparison with Simulations.

According to the Mie theory, light scattering at each wavelength depends on the scattering particle radius, a, and the ratio of the refractive index of the scattering particles, $n_2$, to that of the background medium, $n_i$: $n_i=n_2/n_1$. To establish a reference map of what DRPs could look like depending on the scattering particle radius and the index ratio, the algorithm relying on the Mie theory was used. In one example, the MCRT algorithm (discussed, for example, by Ramella-Roman et al. in *Opt. Express*, 13, 10392-10405, 2005) was employed to simulate a DRP pattern of the polarized light back-scattered by a medium sample with the use of an LSR experimental set up (FIG. 1). The same set-up was later use to procure empirical results for comparison.

In a set-up of FIG. 1, the sample 150 was illuminated by electromagnetic radiation emitted from a source 110 and a high-speed camera 132 was used to capture the temporally fluctuating back-scattered speckle patterns, induced by Brownian movements of scattering particles intrinsically present in the sample 150. The specific embodiment 100 of the experimental set up (configured to operate in reflection, in the backscattering regime), included an illumination portion with a laser source 110 producing output light 110A that, upon passing through an optical train including a linear polarizer 114 and an optional beam expander 118, was directed to the sample 150 through an optical system 120 that contains an optional lens 122 and a beam splitter 124. The sample 150 may be represented, for example, by synovial fluid, vitreous humor, mucus, blood—whether whole blood or individual constituents of blood, bile, or cerebrospinal fluid, to name just a few. In a related implementation, not shown, where the working distance between the lens 122 and the sample 150 was varied, the depth-resolved mapping of the sample 150 could be realized. Optionally, light 110A could be transmitted through an optical fiber 126 prior to traversing the polarizer 114. Time series of images of the sample 150 in light 128 backscattered by the sample 150 was acquired through a polarizer (analyzer) 130 in a detection portion of the system 100 with a high-speed CMOS camera 132 (such as Basler Ace 2000-340 km, Germany) through a lens with adjustable focal length (such as, for example, a focusing lens system MLH-10× by Computar, Commack, N.Y.). The mutual orientation of the polarizer 114 and the analyzer 130 may generally differ depending on the scope of the optical data acquisition, and is not limited to a particular orientation. In the example when the polarizers 114, 130 are linear polarizers, the corresponding transmission axes (viewed along the direction of beam propagation through the polarizers) may be col-linear, perpendicular to one another to form a so-called cross-orientation, or form a different angle. The angle at which the sample 150 is illuminated may differ from the angle at which the detection portion of the system collects light scattered by the sample 150. The use of the CMOS camera 132 to acquire laser speckle patterns from the sample 150 enhanced the statistical accuracy in measuring $g_2(t)$ by simultaneous ensemble averaging of multiple speckle spots, which significantly reduces data acquisition time. The acquired imaging data were stored and processed with the use of a pre-programmed electronic circuitry that included a programmable processor such as a computer processor 136 and tangible non-transitory computer-readable storage medium (not shown), and further optionally displayed for visualization in a required format on a display (not shown). The acquisition of the imaging data representing the sample 150 in light 128 was conducted at a predetermined rate (measured in frames-per-second, fps) to ensure that fast sample dynamics is appropriately detected, during the acquisition time periods (of portions of a second to several seconds). The acquired sequences of speckle patterns could be optionally additionally processed to obtain temporally-averaged irradiance (of a DRP) for a sample's region of interest (ROI) of a chosen size (for example, for about 296-by-296 pixels, which, considering the described optics, corresponds to the field-of-view (FOV) of about 1 mm$^2$). It is appreciated that an embodiment related to that of FIG. 1 can be adapted to operate in transmission (or forward scattering regime), with various states of polarizers 114, 1130 defining different states of polarization of light transmitted through the polarizers, and at different wavelengths. In specific implementations, the set-up may incorporate at least one of a single detector, an array of photodetectors, and pinhole.

In a specific implementation, when the sample 150 under test includes blood and/or its individual constituents, the system may be structured as an optical blood-coagulation sensor disclosed in PCT/US2013/076470 (and, in particular, in reference to FIGS. 10A and 10B of that patent application), and include a sample-carrying cartridge and an optical system containing an array of optical apertures between the sample and the optical detector of the data acquisition portion of the LSR system, which array is used to improve spatial contrast and reduces blurring in the optical data acquired by the detector. The disclosure of PCT/US2013/076470, published as WO 2014/100378, is incorporated herein by reference.

Referring again to the MCRT algorithm, the algorithm was optionally structured to take into account the experimental configuration of the LSR setup 100—such as linearly polarized focused illumination (690 nm), finite slab geometry of the sample 150, and back-reflected (180°) collection of light through the linear polarizer 130. As a result of these MCRT-based simulations, the influence of both a and $n_i$ on the DRP pattern, acquired in linearly polarized light, was established.

In the simulations, the light scatterers of the sample 150 were assumed to be spherical mono-disperse particles with radius values a ranging from about 0.1 microns to about 3 microns, and three refractive-index pairs were used ($n_1$=1.36, $n_2$=1.4, $n_i$=1.03), ($n_1$=1.34, $n_2$=1.5 $n_i$=1.1), and ($n_1$=1.34, $n_2$=1.59, $n_i$=1.2), that covered the range of indices pertinent to various biomaterials and hydrogels of interest. The Mie theory was used to calculate $\mu_a$, $\mu_s'$, and the elements of Mueller matrix, S11, S12, S33, and S34, as discussed below. The concentration of the scatterers in the material was adjusted such that for all cases $\mu_s'$=1.1 mm$^{-1}$. Data input to the MCRT algorithm included known optical properties. The beam of light, incident onto the sample 150, was represented during the calculation by 10$^6$ photons. The incident light was defined to be linearly polarized with the Stokes vector S0=[1 1 0 0]. Upon the photon-particle interactions, the Stokes vector, S, was updated via multiplication with the Mueller matrix. For photons returning to the imaging plane of the camera, the irradiance of light retaining the initial polarization state was calculated using the scalar multiplication of S with S0. The spatial DRP pattern was calculated by spatial binning, which terms refers to creating a 2D-spatial histogram of photon flux components that exhibit a desirable polarization state.

The accuracy of the MCRT simulations was verified experimentally with the use of an optical set-up similar to that of FIG. 1. The empirical data were collected using, as the sample 150, standard aqueous suspensions of polystyrene microspheres ($n_1$=1.34, $n_2$=1.59, providing an a priori knowledge of the index mismatch of $n_i$=1.2). Depending on the experiment, the microspheres had radii ranging from about 0.1 microns to about 3 microns (produced by PolySciences, Inc., Warrington, Pa.). The polybead solutions were diluted to achieve $\mu_s'$=1.1 mm$^{-1}$. One hundred μl of each sample was loaded in an imaging chamber (Grace Bio-Labs Inc., OR) for LSR evaluation. Referring again to the set-up of FIG. 1, light from a polarized laser (690 nm) was collimated and focused via a lens to a 50 μm spot on the sample. The back-scattered speckle patterns were acquired for 0.67 seconds at 753 fps. The DRP patterns were obtained with the use of the LSR modality, and, in one case, by temporally averaging the laser-speckle frames.

The results of the simulations are presented in FIGS. 2A through 2F. Here, each of FIGS. 2A, 2B, and 2C contains a series of five (5) contour plots representing DPR distributions that correspond, respectively, to a=(100 nm, 500 nm, 1000 nm, 2000 nm, 3000 nm). The refractive index parameters for media components used for simulations (the results of which are shown in each of these Figures) are listed at the left-hand side of the DPR distributions, while the scale bars represent the normalized irradiance values.

For comparison with the simulated data of FIG. 2C ($n_i$=1.2), the experimentally measured five DRP patterns (formed by light scattered from polystyrene suspensions) are presented in FIG. 2D. Good agreement between the MCRT-simulated and experimentally measured patterns for a=0.1 . . . 3 μm and $n_i$=1.2 establishes the accuracy of the MCRT method. Both the theoretical and experimental results of FIGS. 2A, 2B, 2C, and 2D convincingly demonstrate that the DPR pattern evolves from a bi-lobular pattern to a clover-like pattern when the scattering particle size is increased.

It can be observed that transformation of the DRPs (for any $n_i$ value) from elliptical (at small values of a) to clover-shaped (at larger values of a) caused by increase in the value of a is accelerated with increase of the $n_i$ value. The DPR pattern evolution may be explained by a transition between the isotropic Rayleigh scattering (effectuated by the smaller particles of low relative refractive indices) to the forwardly-directed Mie scattering (occurring at the larger particles with high refractive index). It is notable that the low index mismatch parameter (on the order of $n_i$=1.03 or so) is characteristic to blood-related fluid or other biological or dairy samples.

Figures 2E, 2F:
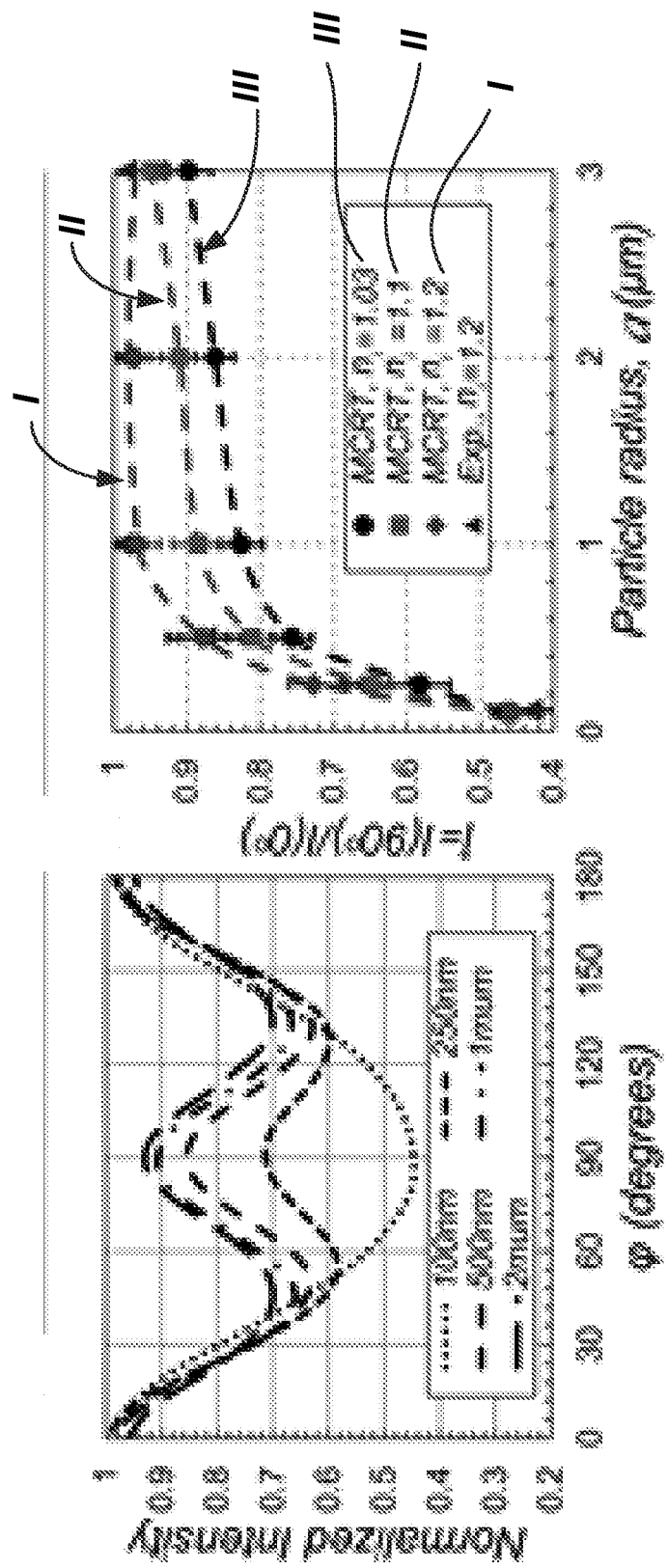
FIG. 2E shows the dependence of normalized irradiance derived from the DRPs vs. the azimuth angle φ for different values of the radius of light scattering particles and $n_i$=1.2, which dependencies were obtained with the use of the MCRT algorithm.
FIG. 2F illustrates the dependence of the ratio of normalized intensities of the DRP, $\hat{I}=I(90°)/I(0°)$ on the radius value a, obtained with the use of the MCRT algorithm as well as from the experiment. Error bars represent standard deviation. The cubic interpolation of the discrete values of $\hat{I}$ on a can serve as the calibration map (expressed as calibration curves) for each $n_i$. The scope of the map is readily expanded for any desired value of $n_i$ and/or any wavelength of light.

As an example, the DRP pattern of FIG. 2C was further used to assess the normalized irradiance of the DRPs vs. azimuth angle, φ, for a: 0.1 . . . 3 μm, and $n_i$=1.2. The dependency of the normalized irradiance of the DRPs are shown in FIG. 2E from which it appears that the ratio of the normalized DRP irradiance values at φ=90° and φ=0° (i.e. $\hat{I}$=I(90°)/I(0°)) may be well suited for describing the change in the DRP pattern from bi-lobular (referred to earlier as elliptical) to clover-shaped. According to an embodiment, therefore, the ratio $\hat{I}$, procured from the series of empirically acquired DRPs from a sample characterized by the $n_i$ value, is used as a quantitative representation of a DRP shape that evolves, for that $n_i$ value, with changes of the light-scattering particle size a. The ratio provides but one example $\hat{I}$=I(90°)/I(0°) of a metric to define the shape of the DRP, Optionally, other metrics could be used such as those including ratios of intensities at different azimuthal angles or even simply the maximum values of intensities at specifically chosen angles.

The example of FIG. 2F illustrates the changes in $\hat{I}$ vs. a derived from FIGS. 2A through 2D (i.e., from the results of both theoretical simulations and the experimentally verified results). The data marked with diamonds and triangles (curve I) corresponding to MCRT simulations and experimental results for a=0.1 . . . 3 μm and $n_i$=1.2 show statistically high correspondence and match. For any $n_i$, the value of ratio $\hat{I}$ grows monotonically as a increases from 100 nm to 2 μm, and eventually reaches saturation. Yet, for a given a, $\hat{I}$ varies by statistically significant 12%, when $n_i$ rises from 1.03 to 1.2, clearly demonstrating that, for correct deduction of a from $\hat{I}$, one has to account for $n_i$. (In comparison, the methodology disclosed in Hielscher et al. (*Appl. Opt.*, 36, 125-135, 1997), for example, simply does not take into account this important parameter.)

Formation of Calibration Map.

To facilitate incorporation of the index mismatch information (expressed, for example, as $n_i$ value) into the process of determination of the a value, a calibration map (or reference map, which may be presented as a set of calibration curves or a calibration/reference table of data) has been formed. Three (3) calibration curves from such set, formed through cubic interpolation of discrete values $\hat{I}$ in this instance for $n_i$=1.03, 1.1, and 1.2 (curves III, II, I, respectively), are shown in dashed lines in FIG. 2F. The calibration curves provide reference points and data for typical small, medium, and large $n_i$ values of specimens tested below and other common biomaterials. In particular, the calibration curves (procured from data representing theoretically simulated dependencies of DRPs on a and $n_i$ and representing the ratio of normalized light irradiance values taken at first and second different values of azimuthal angle) are used to derive the value of a for a given biofluidic sample characterized by a value of $n_i$ that is covered by the calibration map.

Example 1: Determination of Viscoelastic Modulus of a Material

The utility of the proposed methodology for evaluating the viscoelastic moduli of materials with unknown particle sizes using the LSR modality was initially experimentally demonstrated with the use of three common materials in the set-up 100: medicated soap (Steris Corp., Ohio), silicone conditioner (Procter and Gamble, Ohio), and mayonnaise (Kraft Foods, Ill.), all of which were turbid materials with a priori unknown particle size distributions. The samples were loaded in imaging chambers and laser speckle image frames were acquired at 753 fps for 5 seconds. FIGS. 3A, 3B, 3C, and 3D display the respectively-corresponding DRP patterns, along with the normalized irradiance vs. φ plots (curve C, M, S). The differences between the experimental plots of FIG. 3D and the MCRT-generated plots in FIG. 2E are attributed to the differences in optical properties ($n_i$ and $\mu_s'$) and poly-dispersity of the materials, as well as the attributes of experimental factors like camera gain and exposure time.

Figures 3A, 3B, 3C:
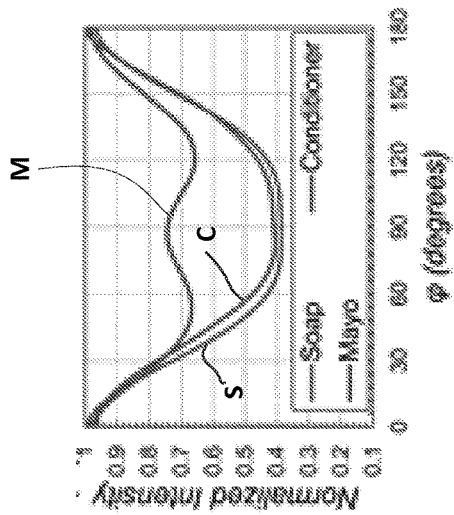
FIGS. 3A, 3B. 3C illustrates experimentally determined DRPs (for soap, conditioner, and mayonnaise, respectively) experimentally determined with transmission axes of polarizers 114, 130 of FIG. 1 being parallel to one another. The side bar represents the pixel irradiance level.
Figure 3D:
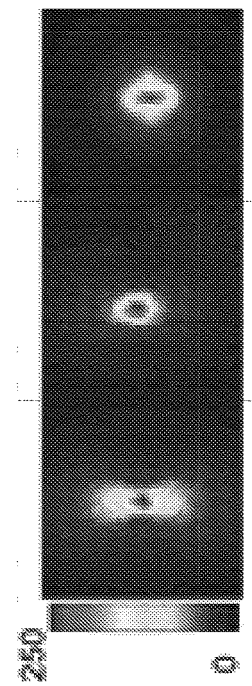
FIG. 3D illustrates a dependence of normalized irradiance vs. angle φ, derived from the DRP images of FIGS. 3A, 3B, 3C. The $\hat{I}$ values $\hat{I}=I(90°)/I(0°)$ are 0.4, 0.42, and 0.77, respectively, and, provided the specified $n_i$ values, scattering particle radii are 0.1, 0.1, and 0.45 µm.

The values of the ratio $\hat{I}$ was determined from the experimentally-acquired plots of FIG. 3D, to be 0.4 (soap), 0.42 (conditioner), and 0.77 (mayonnaise). In these materials, styrene, silica, and fat particles, elicit $n_r$ values of 1.59/1.33=1.2 (soap), 1.46/1.33=1.1 (conditioner), and 1.46/1.33=1.1 (mayonnaise). Accordingly, and in reference to the set of calibration curves the sub-set of three of which (I, II, and III) is plotted in FIG. 2F, one can assess the average a values for soap, conditioner, and mayonnaise to be ~0.1 µm, 0.1 µm, and 0.45 µm respectively. These numbers agree with the published results of measurements carried out with size analyzers (for soap) and electron microscopes (for silicone and fat globules in conditioner and mayonnaise).

Contemporaneously with the determination of the average size of the light-scattering particles, the g2(t) curves are determined based on the same optical irradiance distributions acquired with the optical detector, as known from Our Prior Applications. Such curves, displayed in FIG. 3E, revealed that speckle fluctuations are most rapid in soap and the slowest in conditioner. Radial analysis of DRP (the methodology of which was discussed by Hajjarian and Nadkarni in *PLoS ONE*, 8, e65014, 2013 and *Opt. Express*, 22, 6349-6361, 2014) suggested that for soap, conditioner, and mayonnaise $\mu_a$~0 and $\mu_s'$~1 mm$^{-1}$, 5 mm$^{-1}$, and 14 mm$^{-1}$, respectively. The knowledge of $\mu_a$ and $\mu_s'$ facilitates the deduction of the MSD from the g2(t) curves, as known in the art. The inset of FIG. 3E illustrates that the large and growing MSD values of soap particles vs. time (curve S), which is the characteristic of viscous liquids. In contrast, the magnitude and slope of the MSD are much lower in mayonnaise (curve M) and conditioner (curve C), representing less compliant viscoelastic materials.

Figure 3F:
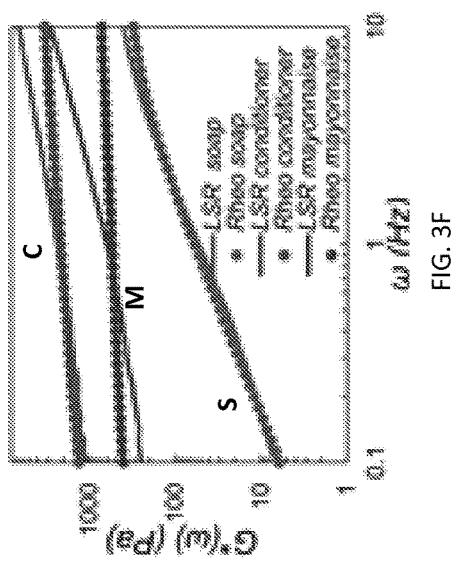
FIG. 3F presents G*(ω) curves obtained from the all-LSR-based measurements incorporating the average size of light scatterers determined with an embodiment of the invention (lines) and mechanical rheometry (dots).
Figure 3E:
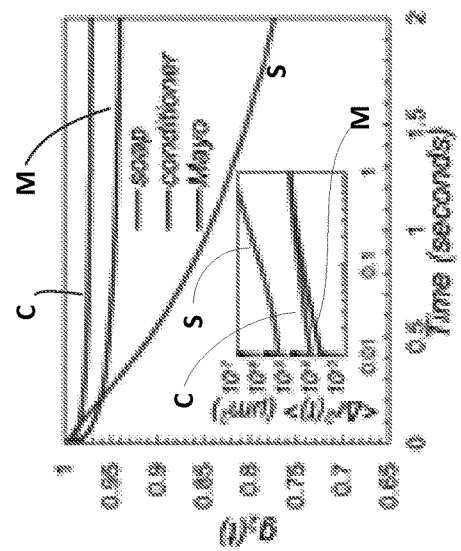
FIG. 3E illustrates autocorrelation curves, g2(t), for soap, conditioner, and mayonnaise. Inset: MSD for light scattering particles in these three materials.

FIG. 3F displays the G*(ω), obtained from the measurements according to the principles of the present invention by using the $g_2$(t)-derived MSD parameters and the a values, experimentally derived as discussed above, in Eq. (1). For comparison, G*(ω) data obtained from mechanical rheometry are also shown. The LSR-derived curves obtained in reliance on particle size (determined with an embodiment of the invention) correspond closely with the conventional mechanical-rheometry results for all samples. At high frequencies, mechanical rheometer results are degraded, as increased inertia inhibits proper shearing of the specimen and the loss tangent, i.e. viscous to elastic moduli ratio, is over-estimated. This is more evident in mayonnaise sample, for which the raw loss tangent increases drastically for ω>1.

Example 2: Determination of Viscoelastic Modulus in Curing Materials or Gels with Time-Varying Mechanical Properties The sensitivity, dynamic range, and limitations of the proposed approach for LSR-based measurements of viscoelastic modulus in curing materials or gels with time-varying mechanical properties were assessed, in this example, during curing of polydimethylsiloxane (PDMS) gels. PDMS1 and PDMS2 samples were prepared by mixing the base and curing agent (Sylgard® 184, Dow Corning, Belgium) in 1:10 ratios. Silica microspheres (PolySciences, Inc.) and Borosilicate beads (Thermo Scientific, Inc. Waltham, Mass.) of two distinct known sizes were added to the precursor mixtures (w/v~10%, and 4%) to induce light scattering. The samples were poured in spectroscopic cuvettes for the LSR measurements. Speckle movies (sets of frames with images of laser-speckles in backscatter) were acquired every 30 minutes for 24 hours at 753 fps for 5 seconds. The remainders of samples were loaded in a mechanical rheometer, and the frequency sweep procedure was conducted in tandem with the LSR measurements, every 30 minutes for 24 hours. The gels fully cured in about 48 hours at room temperature.

FIGS. 3A, 3B displays the DRP images of PDMS1 and PDMS2 samples, respectively. Using approaches discussed in, for example, *PLoS ONE* 8, e65014, 2013, $\mu_s'$=0.9 mm$^{-1}$ and 1.4 mm$^{-1}$ for PDMS1 and PDMS2 were calculated from the DRPs experimentally acquired. FIG. 4C depicts the dependency of the normalized irradiance vs. the azimuthal angle φ, obtained from the DRP images of FIGS. 4A and 4B, as curves 1 and 2. From these curves, the $\hat{I}$ value of 0.67 for PDMS1 and 0.87 for PDMS2 was readily derived. Given the known $n_r$ values of 1.46/1.41=1.03 and 1.56/1.41=1.1 for the PDMS1 and PDMS2, and referring to the set of calibration curves of FIG. 1D, the radii of the scattering particles were determined to be $a_1$~0.25 µm and $a_2$~0.75 µm for silica and borosilicate beads, respectively (which closely agrees with manufacturer specifications ~0.25 µm and 1±0.25 µm). The time-lapsed g2(t) curves presented in FIGS. 4D and 4E demonstrate the rate of speckle fluctuation during the curing of the PDMS as a function of time. Using the $\mu_s'$ values, the time-dependent MSD for the PDMS1 and PDMS2 samples was derived from the g2(t) curves and shown in insets of FIGS. 4D and 4E, respectively.

The time-lapse all-LSR based measurements of the G* modulus, evaluated at ω=0.2 Hz by taking into account the values of the average size of the light scatterers as discussed above, are shown in solid lines in FIG. 4F and compared with the results procured with the conventional mechanical rheometer (shown with dots). The LSR measurements agree well with mechanical rheology results and accurately follow small increments of G*, on the order of few Pa, as PDMS gel transforms from a low viscosity liquid to a primarily elastic solid with G* ~10 kPa. It is notable that beyond, the gel point (located beyond 10 hours from the moment of the start of curing), the viscosity of PDMS converges to infinity and induces a primarily elastic solid with frozen and non-ergodic speckle dynamics. In this region, the sensitivity of the LSR modality to changes in elastic properties is somewhat limited and effects of CMOS sensor noise may confound the results of the measurements. Stated differently, the results of the all-LSR measurements may deviate from the mechanical rheology results during later phases of curing. However, our prior studies indicate that in biphasic biological tissue speckle dynamics remain fully fluctuating and ergodic even for G*~600 kPa and LSR maintains a dynamic range over 7 decades of moduli (see, for example, Hajjarian and Nadkarni, *Sci. Rep.*, 2, 316, 2012).

Figure 5:
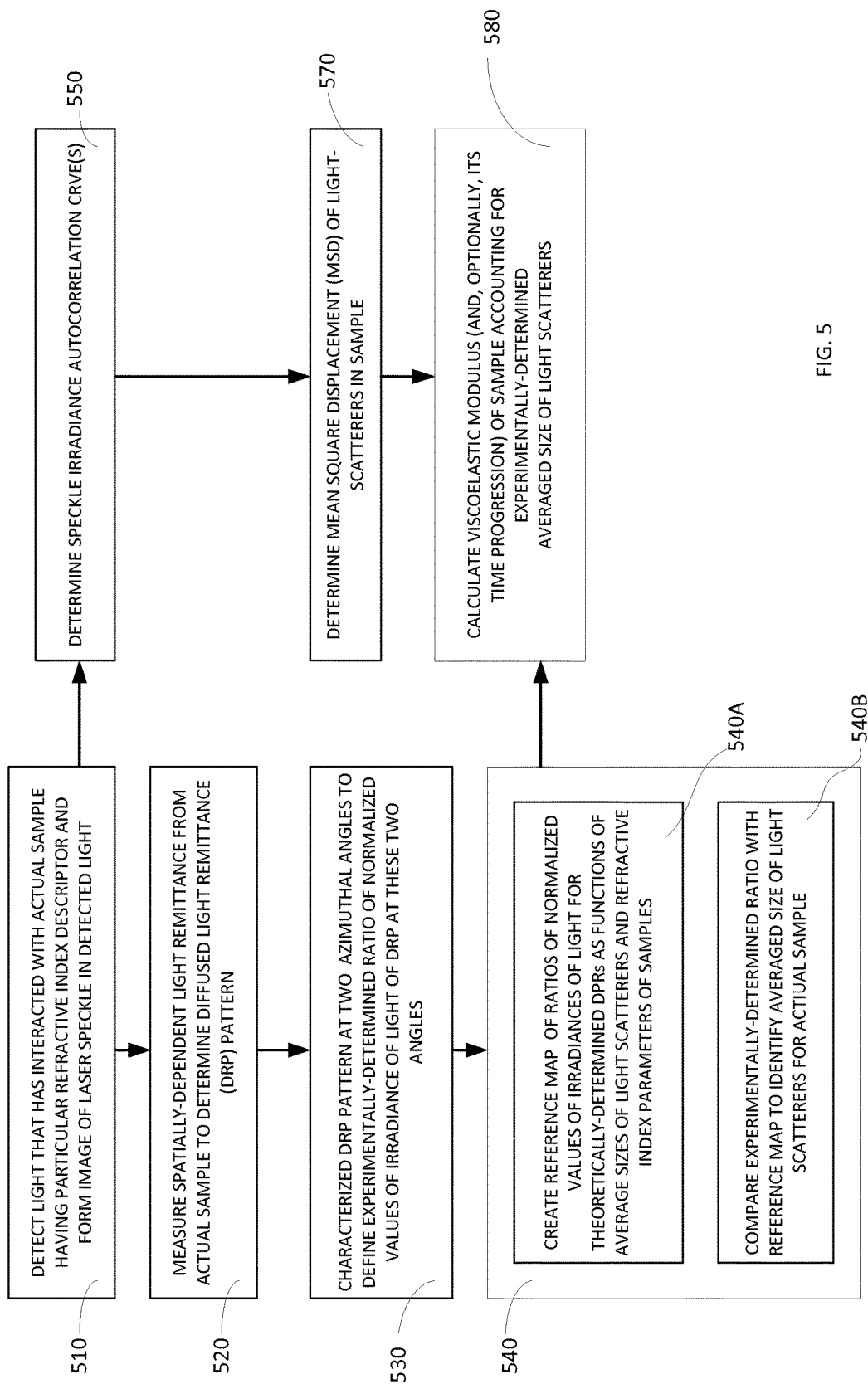
FIG. 5 is a flow-chart illustrating schematically an embodiment of the method of the invention.

FIG. 5 provides an example of a flow-chart illustrating, schematically, an all optical method of determination of a viscoelastic parameter of a sample under test (SUT; such as a biofluidic sample, for example) carried in reliance on experimental data acquired exclusively with the use of the same, single optical system. In the example of FIG. 5, at step 510, light that has interacted with a sample (including light-scattering particles in the hosting medium and characterized by $n_r$) and that is scattered by the sample is acquired with an optical detection unit. At least one image of the detected light distribution is formed. In one case, light may have high degree of optical coherence and the detected light distribution may correspond to a laser-speckle. At step 520, the determination of light remittance (as a function of a spatial coordinate, such as a linear angle in the plane of the optical detector) is made to derive a DPR pattern based on the formed optical image(s). At step 530, a descriptor of the experimentally-determined DPR pattern defined, in one specific example, as an experimental ratio of two normalized values of light irradiance (each corresponding to a different spatial coordinate—for example, two normalized values of light irradiance corresponding to two values of an angle), is determined. At step 540, the determination of the averaged size of the light scatterers in the SUT is carried out. The determination of such averaged size at step 540 may be carried out by a) forming, at step 540A, a reference map of reference ratio values extracted from the reference DRPs. The reference DRPs are theoretically calculated for the variety of the speckle fields that are also determined analytically for the variety of light scatterers of different sizes and different refractive indices hosted in media having different background refractive indices; and b) determining, at step 540B, which average size of the scatterers corresponds to a point, on that reference map, that represents the descriptor of the experimentally-determined DPR pattern. The averaged size of light scatterers, determined from the input optical data, is further incorporated into the generalized Stokes-Einstein relation (GSER) to determine the viscoelastic modulus at step 580 with the use of the MSD data obtained, at step 570, from the same input optical data via speckle irradiance autocorrelation curves as a result of processing the optical images at step 550.

It is appreciated that when a biofluidic sample is used (which includes blood or its individual constituents), the time-dependent change of the viscoelastic modulus, calculated with the use of the so-determined averaged size of the blood-sample light-scatterers, can be further utilized for determination of parameters of (blood) coagulation cascade (and, in particular, clotting time and at least one of total coagulation time, clot formation time, maximum clot firmness, maximum lysis, clot kinetics, percentage of lost clot stability at a selected point in time, rate of clotting, fibrinolysis time, clot compliance, and clot viscosity) as disclosed, for example, in U.S. Pat. No. 8,772,039 the disclosure of which is incorporated herein by reference. The biofluidic sample containing whole blood or its constituents may include a stationary sample and, in particular, an in-vivo non-circulating sample. In the alternative, a method for determining the scattering particle size may be optionally employed with circulating (or moving) samples, such as flowing blood, circulating fluids and the like.

It has been disclosed, therefore, that the procedure of determination of light-scattering particle size (rooted in the analysis of the diffusive remittance profile of the SUT, which profile is determined with the use of image(s) of the laser speckle produced by the SUT test) is fully incorporated in and operably cooperated with the optical modality and does not require additional instrumentation to enable accurate evaluation of the viscoelastic moduli of the SUT with high sensitivity over a large range of modulus values. The MCRT simulations and experimental results discussed above suggest at least that this approach may be used to precisely determine the average scattering sizes in the order of 0.1 . . . 2 μm, with the use of light at a single wavelength (in this case, 690 nm), corresponding to Rayleigh-Mie scatterings transition regime. The particle size determination is wavelength-dependent and using longer wavelengths such as, for example, 1300 nm, particles sizes of up to 10 nm and larger may be measured. The proposed DRP-based particle sizing methodology is primarily appealing for use during the measurements of biomaterials, where the refractive index mismatch between the light-scatterers and the hosting medium is small. For inorganic scatterers of higher refractive indices a distinct set of DRP calibration curves may be required.

Related Embodiments

Figure 6:
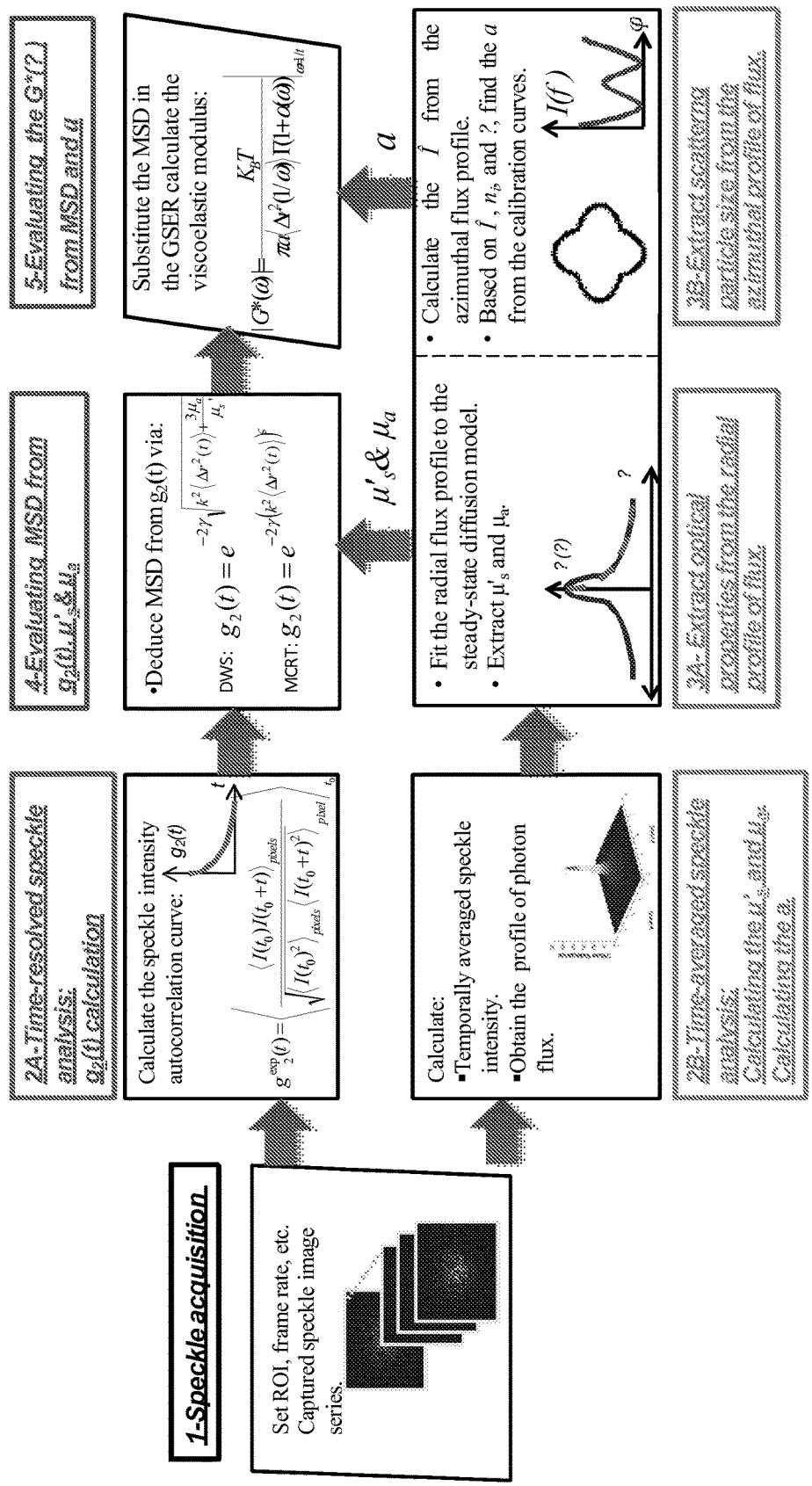
FIG. 6 is a flow chart representing an embodiment of the processing algorithm according to the invention.
Figure 7C:
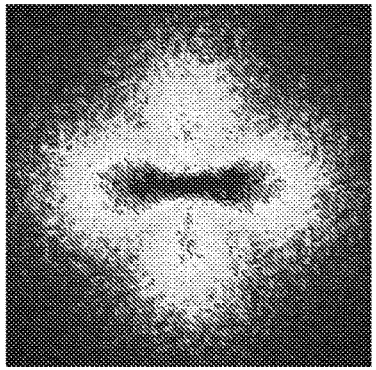
FIGS. 7A, 7B, 7C, 7D and 7E are theoretically calculated (with the use of the MCRT algorithm) DRPs for samples containing intrinsic light scatterers with radii a=3 µm, and $n_i$ values of 1.03. The plots represent DRPs obtained by illuminating a sample with a one wavelength-tunable source or multiple individual lasers with varying wavelengths between 633 nm and 1300 nm. The vector of polarization of light incident on the samples is parallel to samples' surfaces.
Figure 7B:
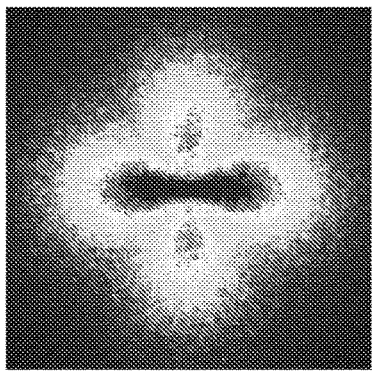
Figure 7E:
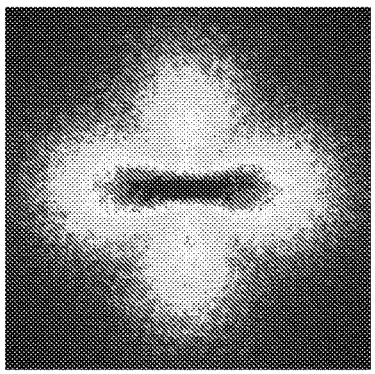
Figure 7A:
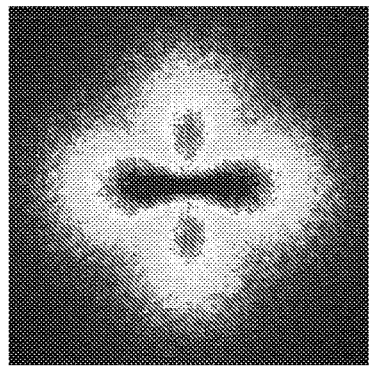
Figure 7D:
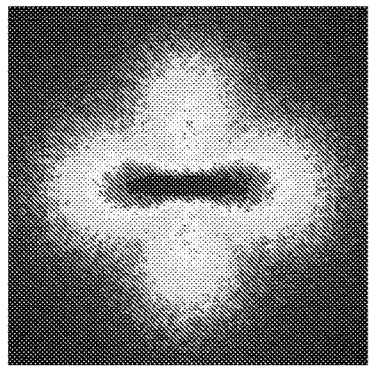

A related embodiment of the processing algorithm, schematically shown in FIG. 6, was employed to process a series of optical irradiance distributions detected in light scattered by the material at hand and to deduce the complex viscoelastic modulus of such material. As discussed before, temporally-resolved and temporally-averaged processing was conducted on the speckle images acquired with the LSR apparatus (similar to that of FIG. 1). The laser-speckle images (caused by coherent illumination of the sample) or diffused reflectance images (caused by speckle time averaging or sample irradiation using coherent or incoherent radiation) may be acquired at multiple wavelengths and/or multiple polarization states.

As illustrated in Box 2A of FIG. 6, the temporally-resolved correlation analysis of speckle images yields the speckle intensity autocorrelation function, $g_2(t)$. This processing may be performed using, for-example, electronic circuitry such as that including a programmable computer processor with the use of appropriate software (such as for instance MATLAB and C++). Alternatively, specialized hardware and processors, such as for instance programmable digital correlators, may be used to calculate the acquired $g_2(t)$ curves at the hardware level.

Box 2B of FIG. 6 describes that temporal-averaging of the speckle images yields the diffuse profile of the remitted flux. This process may be conducted by temporally averaging the same speckle frame series that are subject to temporally-resolved correlation analysis. Alternatively, capturing a single speckle image with sufficiently long exposure time may also provide the diffuse profile of the remitted flux.

Box 3A of FIG. 6 illustrates that the diffuse remitted flux may be sectioned radially and averaged over various azimuth angles to calculate the radial profile of the flux. Next, optical properties, such as for example reduced scattering coefficient, $\mu_s'$, and absorption coefficient, $\mu_a$ are calculated by fitting a proper curve obtained from the steady-state diffusion theory to the radial profile of the diffuse remittance.

Subsequently, as elaborated in Box 4 of FIG. 6, MSD is derived from speckle intensity autocorrelation curve and optical properties, with the use of a DWS formalism. Alternatively, MSD may be derived from speckle intensity autocorrelation curve and optical properties using the MCRT-derived formalism, such as the ones elaborated by Hajjarian and Nadkarni in *PloS ONE*, 8, e65014, 2013, which is incorporated by reference herein.

Box 3B of FIG. 6 illustrates that the diffuse remitted flux may be sectioned azimuthally and averaged over various radial directions to calculate the azimuthal profile of the flux. The azimuthal profile of the flux is then depicted versus azimuth angle, φ. Next the ratio of the irradiances at the first angle to the one at the second angle are calculated: $\hat{I}=I(\varphi_1)/I(\varphi_2)$, where in one instance $\varphi_1$ is equal to for example 90° and $\varphi_2$ is equal to for example 0°. Alternatively, as discussed below, $\varphi_1$ and $\varphi_2$ may take on different values based on the arbitrary set of illumination and detection polarization states.

Next, data representing the size of a scattering particle in the sample (such as for example average scattering particle size, a, and a poly-dispersity index, PDI) is calculated in reference to the corresponding calibration curves (discussed as maps in reference to FIG. 2F) for the known values of illumination wavelength, λ, and refractive index mismatch, $n_r$.

Box 5 of FIG. 6 illustrates that the data for MSD and a are used in the generalized and modified Stokes Einstein equation (Eq. 1) to calculate the $G^*(\omega)$.

Notably, the sample may be illuminated by electromagnetic radiation at a single wavelength, or by using a wavelength-tunable laser source such as a tunable laser with the tunable range from about 633 nm to about 1300 nm. Alternatively, multiple different laser sources of various wavelengths or a single broadband source may be used to illuminate the sample in a predetermined order. Alternatively, optical filters may be used to preferentially select a single wavelength or multiple wavelengths for illumination. As will be understood from the discussion presented below, using multiple wavelengths for laser-speckle imaging extends the scope of DRP-based particle sizing by increasing the size range over which scattering particle size can be measured. In other words, by using multiple wavelengths, a wider range of scattering particle sizes may be retrieved from the speckle images. Moreover, it may enable estimating the scattering particle size distribution and its parameters in materials containing particles of various, non-uniformly distributed sizes. An example of such parameter may be a poly-dispersity index (PDI). In addition, this method may allow determination of different particle sizes within the same sample. One example of this application is the determination of lipid particle size in blood or blood components including serum and plasma. Another example may include determination of sizes of different blood cells including red blood cells, white blood cells including platelets, lymphocytes, monocytes neutrophils and others.

The potential of multi-wavelength illumination and detection in an embodiment of the invention is illustrated in FIGS. 7A, 7B, 7C, 7D, and 7E. Here MCRT-simulated DRPs remitted from a sample containing light scattering particles with radius of a=3 μm and characterized by a refractive index mismatch of $n_i$=1.03 are shown. The calculation was based on assumption of the sample being illuminated with light from various laser sources at wavelengths 633 nm, 800 nm, 1000 nm, 1100 nm, and 1300 nm. The vector of polarization of light incident on the material was assumed to be parallel to sample's surface. A skilled artisan will readily appreciate that as the wavelength increases, the DRP changes its shape from the clover-like shape to a bi-lobular shape. In other words, the second and fourth lobes forming the clover shape fade away with increase in wavelength, allowing to conclude that the shape of the DRPs depends not only on scattering particle size and refractive index mismatch but also on the illumination wavelength. This effect is attributed to the reduction of a/λ, and the resulting transition between Mie and Rayleigh scattering regimes.

Figures 8A, 8B:
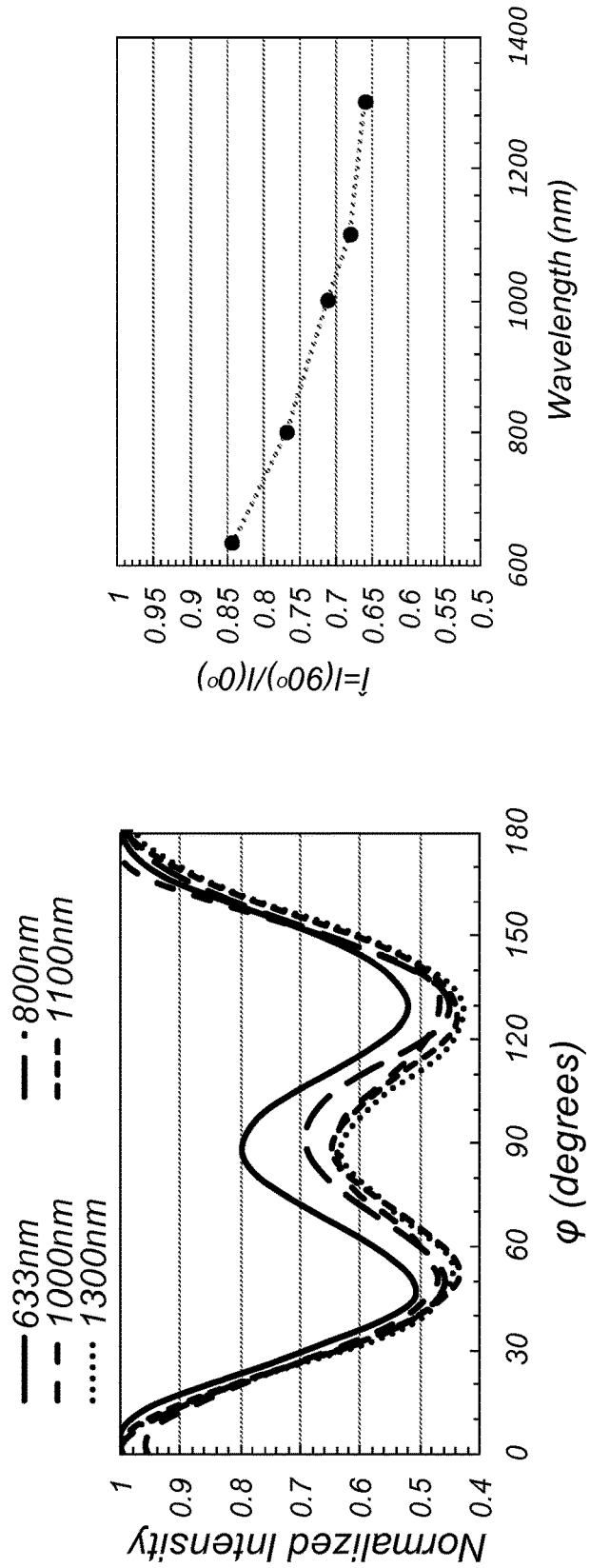
FIG. 8A shows a dependence of normalized irradiance profiles derived from the DRPs of FIGS. 7A-7E as a function of the azimuth angle φ for a fixed values of the radius of light scattering particles, a=3 µm, and a fixed value of $n_i$=1.03; obtained with the MCRT algorithm.
FIG. 8B is a plot representing a dependence of the ratio $\hat{I}$ of normalized irradiances of the DRPs of FIGS. 7A-7E on the illumination wavelength ranging between 633 nm-1300 nm, obtained with the use of the MCRT algorithm.

In one embodiment, to extend the DRP-based particle sizing approach and to obtain additional calibration curves (map), with linear range beyond a=3 μm (which was shown in FIG. 2F), the data representing DRPs of FIGS. 7A through 7E were processed to obtain the normalized irradiance vs. azimuth angle, φ, dependencies for a=3 μm, and $n_i$=1.03, at multiple wavelengths within the wavelength range between 633 nm and 1300 nm. By analogy with the approach discussed in reference to FIG. 2F, the ratio of the normalized irradiance at φ=90° and φ=0° (i.e. Î=I(90°)/I(0°)) (or, alternatively, the ratio calculated at other angles for example at I(120°)/I(30°), I(180°)/I(45°), or another appropriate values of angles) is further procured as a quantitative representation of evolution of the DRP shape for given a and $n_i$ values, with changes of the illumination wavelength, λ. FIG. 8B depicts a calibration map (or reference map, which may be presented as a set of calibration curves or a calibration/reference table of data) by displaying the ratio of normalized irradiances of the DRPs, Î, obtained from the data of FIG. 8A as a function of illumination wavelength ranging between 633 nm and 1300 nm. It is evident that as the wavelength increases, Î decreases. In comparison with methodologies employed in related art it is appreciated, therefore, that the process of determination of the a value should preferably take into account not only the index mismatch characteristic of the sample, $n_i$, but the wavelength of the illuminating light as well.

Given the wavelength dependence of DRP patterns, multiple calibration curves, similar to the ones presented in FIG. 2F may be obtained by changing the illumination wavelength. For example FIGS. 9A, 9B, 9C, 9D, 9E, and 9F display the contour plots of remitted DRPs, simulated with the use of MCRT, for different values of the radius of light scattering particles (a=100 nm, 500 nm, 1000 nm, 2000 nm, 3000 nm, and 4000 nm) and $n_i$=1.03, at the illumination wavelength of 1300 nm. When compared to the simulated DRPs of FIG. 2A (obtained for identical particle sizes and refractive index characteristic), the trend of DRP evolution from the bi-lobular shape to clover-like pattern has slowed down significantly. This is attributed to the longer illumination wavelength, and the correspondingly smaller ratio of a/λ, which slows down the transition between the Rayleigh and Mie scattering regimes.

Figure 9A:
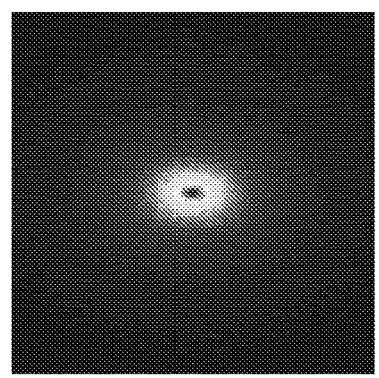
FIGS. 9A, 9B, 9C, 9D, 9E, and 9F show dependencies of normalized irradiance profiles derived from the DRPs vs. the azimuth angle φ for different values of the radius of light scattering particles and $n_i$=1.03, for the illumination wavelength of 1300 nm. These dependencies were calculated with the use of the MCRT algorithm.
Figure 9B:
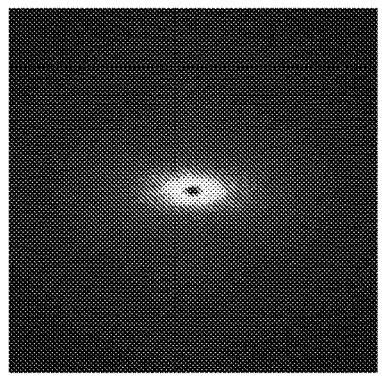
Figure 9C:
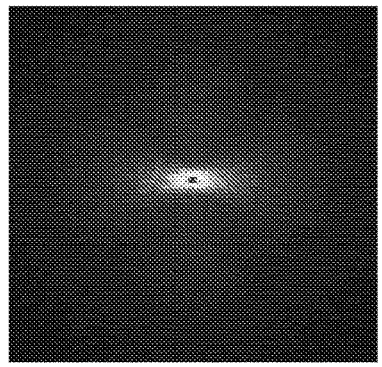
Figure 9D:
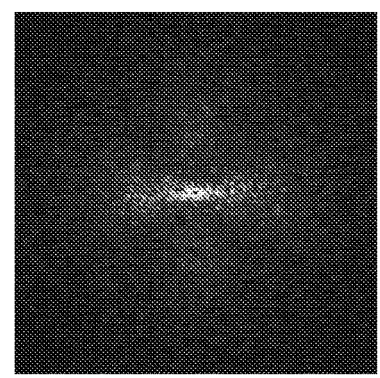
Figure 9E:
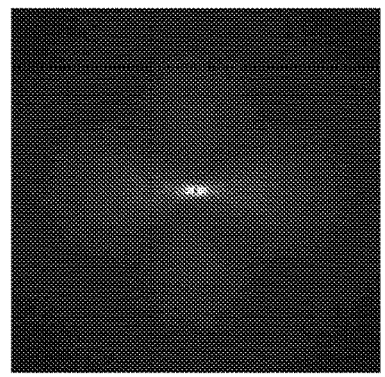
Figure 9F:
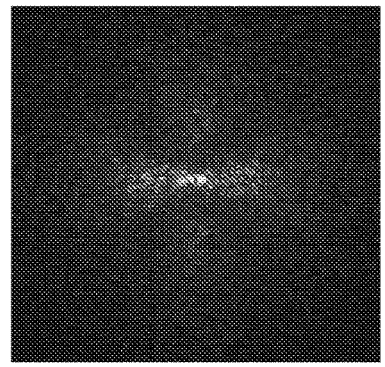
Figure 9G:
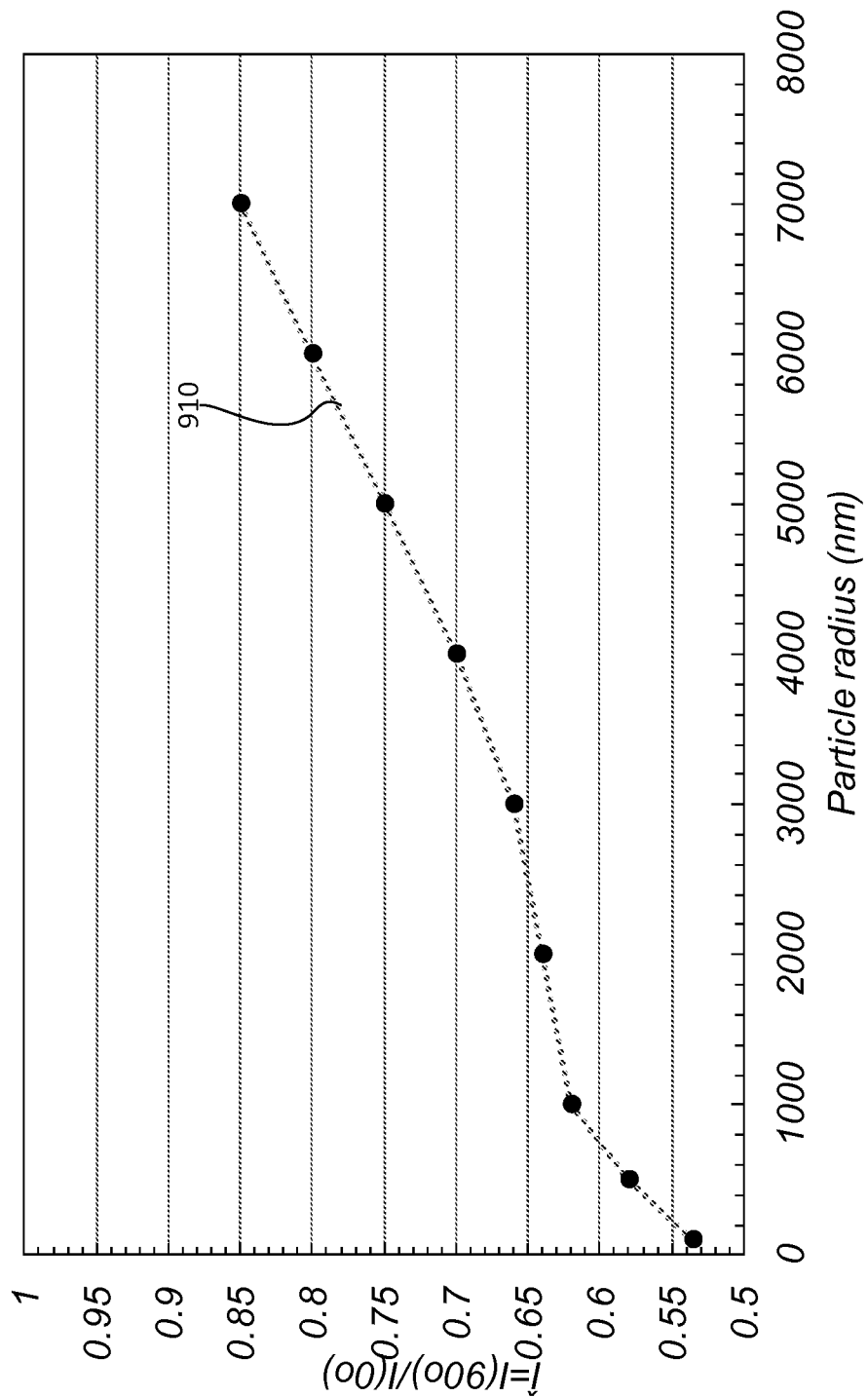
FIG. 9G is a plot with the dependence of the ratio $\hat{I}$ of normalized irradiances of the DRPs on the radius value a, obtained with the use of the MCRT algorithm for the illumination wavelength of 1300 nm. The scope of the map is readily expanded for any desired value of $n_i$.

FIG. 9G illustrates the expected Î values obtained from the DRP images of FIGS. 9A through 9F as a function of scattering particle size radius a, calculated with the use of the MCRT algorithm for the illumination wavelength of 1300 nm. While the map of FIG. 9G is presented only for $n_i$=1.03, the scope of the map may be readily expanded for any desired value of $n_i$. Notably, the linear range of the calibration curve 910 is extended at λ=1300 nm, permitting the particle size estimation beyond the range achievable, with the use of a single wavelength, from the calibration curves of FIG. 2F.

In another related embodiment, the process of acquisition of optical data and the process of determination of the scattering particle size and the viscoelastic modulus value is substantially extended by operating light (that illuminating the sample and that collected by the optical detector) in one or more predetermined polarization states (such as for example, linear polarizations that are, relatively, Horizontal, Vertical, at +45°, at −45° in a chosen system of coordinates; or example right hand and left-hand circular or even elliptical polarization). The incident and detected polarizations states may be parallel or perpendicular to one another or, generally, these states may be in a different angular relationship. In practice, and in reference to FIG. 1, the polarization state of light incident onto the sample 150 may be varied manually using, for example, a simple polarizer-filter turret or wheel or alternatively in an automatic fashion with the aid of a programmable spatial light modulator (SLM), other tunable polarization modulators (for instance a photoelastic, electro-optic modulators, or liquid-crystal-based optical modulators), or an electronic circuitry configured to govern the spatial orientation of a polarizer. Similarly, on the side of the optical detector 132, the remitted speckle images may be collected at different polarizations states either manually or automatically, using for example either polarizer wheel or other polarization dependent detectors and detection methods.

As long as the states of polarization of illuminating and detected light are equal, the detected DRP patterns are substantially identical to the ones collected with the use of two linear polarizers as polarizers 114, 130), except for an arbitrary rotation angle which may also be used to detect DRP and measure particles sizes accordingly.

The examples of DRP patterns for multiple transmission/detection polarization state pairs are shown in FIGS. 10A through 10I, 11A through 11I, and 12A through 12I. FIGS. 10A, 10B, 10C, 10D, 10E, 10F, 10G, 10H, and 10I depict experimentally determined DRPs for Half & Half milk product with polarization states defined by polarizers 114, 130 as Horizontal-Horizontal (H-H), FIG. 10A; Horizontal-Right Hand Circular (H-RHC), FIG. 10B; Horizontal-Vertical (H-V) (Perpendicular to one another), FIG. 10C; Left Hand Circular-Horizontal (LHC-H), FIG. 10D; Left Hand Circular-Right Hand Circular (LHC-RHC) (Perpendicular states of polarization), FIG. 10E; Left Hand Circular-vertical (LHC-V), FIG. 10F; Right Hand Circular-Horizontal (RHC-H), FIG. 10G; Right Hand Circular-Right Hand Circular (RHC-RHC) (co-polarized measurement), FIG. 10H; Right Hand Circular-Vertical (RHC-V), FIG. 10I.

It is readily recognized that as long as the polarization states of the illuminating and detected light are the same (co-polarized), the DRP patterns look the same except for a constant predictable rotation angle and a scaling factor that depend on the initial polarization state of the source of light 110. FIGS. 10C and 10E also illustrate that when the state of polarization of the illuminating and detected light are perpendicular to one another (cross-polarized), the DRP patterns are often clover-like and identical to one another except for a known constant rotation angle. When the angular relationship between the polarization states of the illuminating and detected light is determined otherwise, the remitted DRP is likely a weighted superposition of the co-polarized and cross-polarized scenarios.

FIGS. 11A, 11B, 11C, 11D, 11E, 11F, 11G, 11H, and 11I depict experimentally determined DRPs for Intralipid for polarization states of the polarizer 114 and the analyzer 130 identified as H-H, H-RHC, H-V, LHC-H, LHC-RHC, LHC-V, RHC-H, RHC-RHC, and RHC-V, respectively. It can be recognized from FIGS. 11A and 11H that as long as the illuminating and detected light beams are co-polarized, the DRP patterns look identical except for a constant predictable rotation angle and perhaps a scaling factor. From FIGS. 11C and 11E, a skilled artisan will appreciate that when the illuminating and detected light beams are cross-polarized, the DRP patterns are always clover-like and identical to one another except for a known constant rotation angle. When polarization states of the illuminating light and the detected light are in a different angular relationship, the remitted DRP is likely a weighted superposition of the co-polarized and cross-polarized scenarios.

FIGS. 12A, 12B, 12C, 12D, 12E, 12F, 12G, 12H, and 12I depict experimentally determined DRPs for Blood with for polarization states of the polarizer 114 and the analyzer 130 defined as H-H, H-RHC, H-V (Perpendicular to one another), LHC-H, LHC-RHC (Perpendicular to one another), LHC-V, RHC-H, RHC-RHC (Parallel to one another), and RHC-V, respectively. From FIGS. 12A and 12H one can conclude that as long as the illumination and detection light beams are co-polarized, the DRP patterns look identical except for a constant predictable rotation angle and perhaps a scaling factor. From FIGS. 12C and 12E, one can appreciate that when the illuminating and detected light beams are cross-polarized, the DRP patterns are always clover-like and identical to one another except for a known constant rotation angle. When polarization states of the illuminating light and the detected light are relate to each other in a different fashion (for example, the angle formed by the vectors of corresponding polarizations are neither zero nor 90 degrees), the remitted DRP is likely represented by a weighted superposition of the co-polarized and cross-polarized scenarios.

In most biological samples and industrial polymers, scattering particles do not poses identical sizes and these turbid materials are not mono-dispersed. Rather, most naturally occurring turbid specimens are poly-dispersed materials, in which the scattering particles of multiple sizes exist and, therefore, the scattering particle size has a wide distribution. Dispersity (or a degree of dispersity) is referred to, herein as a measure of the heterogeneity of scattering particles size in the specimen. The poly-dispersity index (PDI) is used to quantify the normalized width of the scattering particle size distribution. This metric can be defined, for example, as $PDI = \sigma_a/\mu_a$, where $\mu_a$ and $\sigma_a$ are the mean and the standard deviation of particle size distribution. Poly-dispersity and the wide particle size distribution in biological materials potentially influence the detected DRP patterns and the calibration curves. The methodology employed so far addresses the use of mono-disperse standard particles of identical size, a, and refractive index mismatch, $n_i$, and investigates the influence of both a and $n_i$ and wavelength on the reflected DRP patterns and derive the calibration curves (see sets of FIGS. 2, 8, and 9). A related embodiment of the invention turns on addressing the effect of poly-dispersity of materials on light scattering in a similar fashion. In poly-disperse materials, the detected DRP may be represented by a superposition of DRP patterns formed by subsets of scattering particles with identical sizes (for example, as a weighted sum of DRPs based on the number density and scattering cross-section of light-scattering particles). As a result, for instance, the total $\hat{I}$ (such as $I(90°)/I(0°)$) represents the average of $\hat{I}$ calculated form overlaid DRPs. Since averaging is a linear operation, the calibration curves (maps) of FIGS. 2, 8, and 9 are applicable in the case of poly-disperse materials and the particle size estimated using these maps is the averaged scattering particle size. It is noted that the process of averaging has a low-pass filtering effect. Therefore, it is possible that the width of a lobe and curvature of the overall averaged DRP pattern do not match exactly the pattern corresponding to a mono-disperse material with the equivalent particle size. In addition, individual particle sizes of polydispersed materials may also be estimated by the wavelength scanning technique described above.

To better illustrate the effects of poly-dispersed particles with unknown particle size distributions on LSR results, the polarized Monte-Carlo Ray Tracing algorithm discussed by J. Ramella-Roman et al. (Three Monte Carlo programs of polarized light transport into scattering media: part I," *Opt. Express*, vol. 13, pp. 4420-4438, 2005) was modified to incorporate the influence of poly-dispersity of materials. Assorted particle size distributions were used to calculate the average scattering particle size and corresponding standard deviation, as well as optical properties and the elements of Muller matrix. Based on the modified polarized MCRT algorithm, the DRP patterns remitted from the aforementioned poly-dispersed materials were then calculated.

Figure 13A:
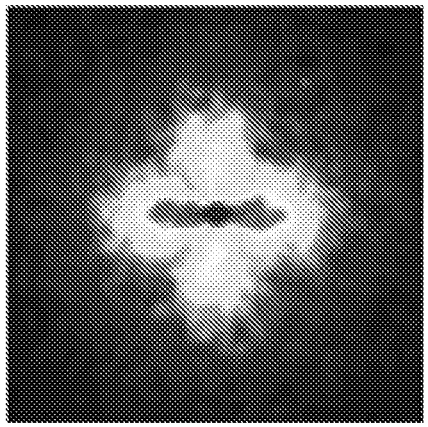
FIGS. 13A, 13B, and 13C illustrate DPRs (theoretically calculated with the use of the MCRT algorithm) for samples containing intrinsic light scatterers with average radius value of a=3 µm; poly-dispersity indices of 0, 0.1, and 0.5; and $n_i$ values of 1.03. In such calculations, it was assumed that samples were illuminated with laser light at 633 nm. The vector of polarization of light incident on the material is parallel to samples' surfaces. Dispersity is a measure of the heterogeneity of scattering particles size in the specimen. The poly-dispersity index (PDI) quantifies the normalized width of scattering particle size distribution and can be defined, for example, as PDI=$\sigma_a/\mu_a$, where $\mu_a$ and $\sigma_a$ are the mean and the standard deviation of particle size distribution.
Figure 13B:
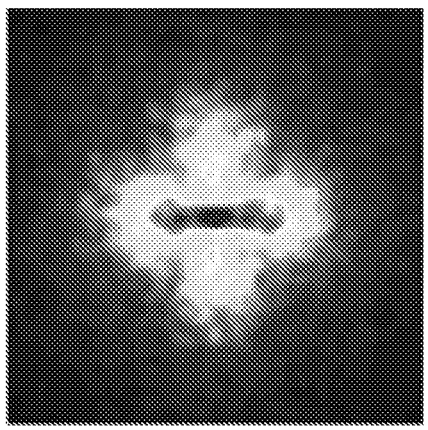
Figure 13C:
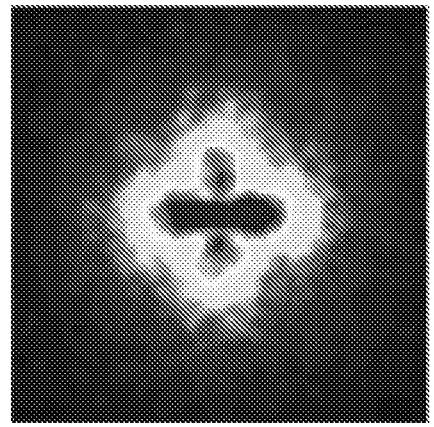

FIGS. 13A, 13B, and 13C illustrate the calculated theoretically (with the use of the polarized MCRT algorithm modified according to an embodiment of the invention to account for poly-dispersity) DRPs for samples containing intrinsic light scatterers with equal average scattering particle size, $\mu_a = 3$ μm, and $\sigma_a = (0; 0.3$ μm; and $1.5$ μm). For all three samples, $n_i = 1.03$ and it was assumed that the samples were illuminated with laser light at 633 nm. The vector of polarization of light incident on the material is parallel to samples' surfaces, for all three samples. However, the PDIs for these samples were chosen to be different: 0 in case of FIG. 13A; 0.1 in case of FIG. 13B; and 0.5 in case of FIG. 13C. The results indicate that increasing the PDI increases the width of a love of the DRP pattern is increased with the increase of the PDI.

The discussed methodology of the invention is applicable to a range of samples, including industrial polymers, dairy products, biological samples and other samples of varying stiffness and mechanical properties. For instance, FIGS. 14A, 14B, 14C, 14D, 14E, 14F, 14G, 14H, 14I, 14J, 14K, 14L, 14M illustrate DRPs (for Intra-lipid, Half & Half, Butter, Synovial Fluid, Vitreous Humorous, Bile, Blood, Plasma, Cartilage, Calcific Plaque, Fibrous Plaque, Lipid-rich Plaque, respectively) that were experimentally determined with the use of the polarizer 114 and the analyzer 130 the transmission axes of which were parallel to one another.

Elements of Mie Theory, Stokes Vectors, MCRT Ray-Tracing.

Figure 15B:
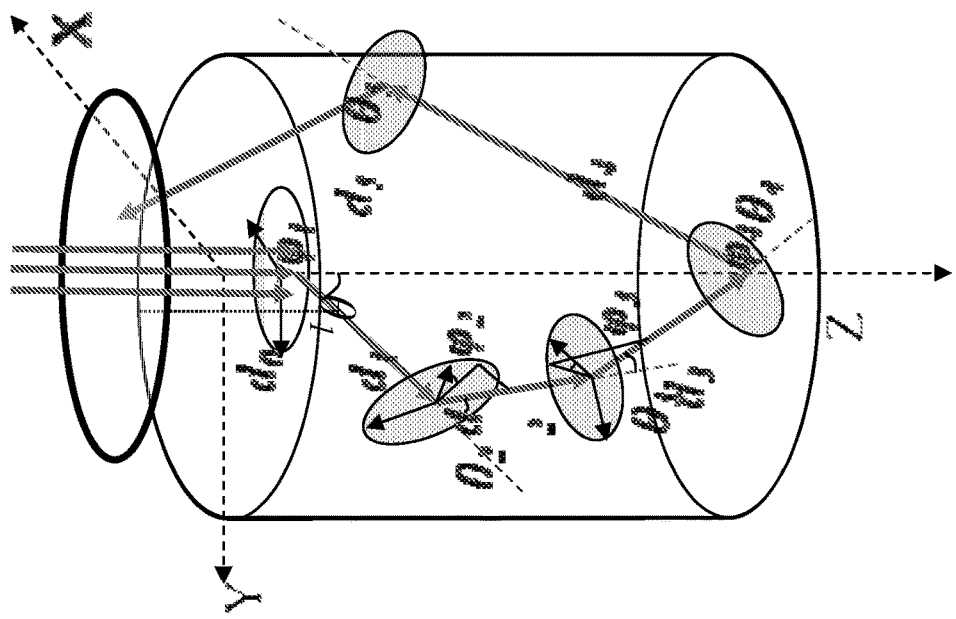
FIG. 15B is a pictorial schematic of Monte-Carlo ray tracing used to simulate the polarized diffuse remitted flux.
Figure 15A:
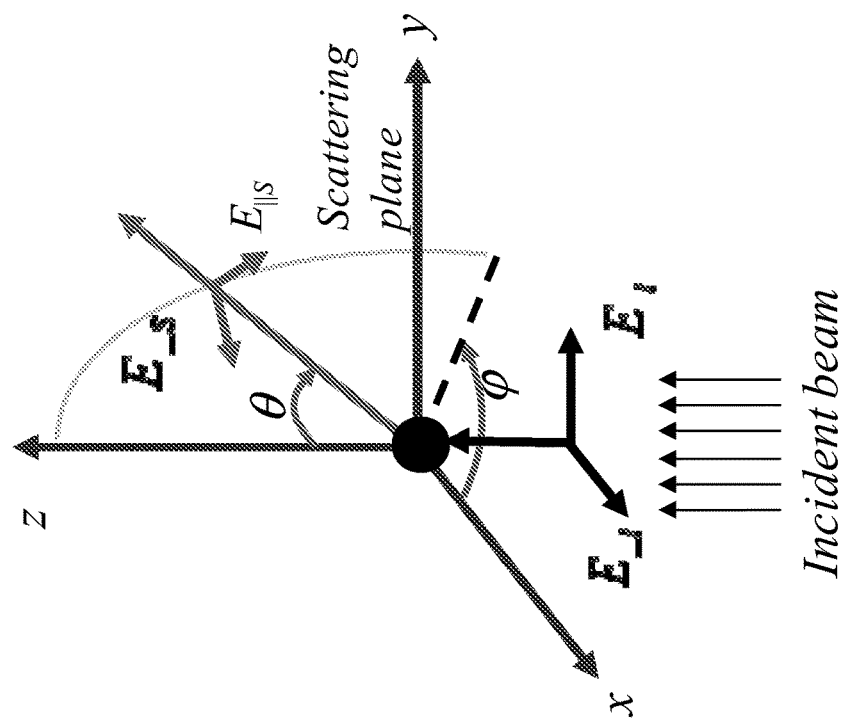
FIG. 15A is a diagram illustrating schematically light scattering by intrinsic light scattering particles of a sample in accord with the Mie theory of scattering.

FIG. 15A provides a diagram illustrating the scattering of polarized light by a particle. Light scattering by particles that have dimensions comparable to the incident beam wavelength is described by the Mie theory, which yields the scattered electric field, exhibiting parallel and perpendicular polarization states as a function of incident parallel and perpendicularly polarized electric field as:

$$\begin{bmatrix} E_{\|S} \\ E_{\perp S} \end{bmatrix} = \frac{e^{jk(R-z)}}{-jkR} \begin{bmatrix} S_2(\theta) & 0 \\ 0 & S_1(\theta) \end{bmatrix} \begin{bmatrix} E_{\|i} \\ E_{\perp i} \end{bmatrix} \quad (2)$$

As depicted in FIG. 15A, the solution for the scattered electric field is given in terms of two scalar components $S_1(\theta)$ and $S_2(\theta)$, which are functions of incident field polarization state (with respect to scattering plane the plane in which $\theta$ is measured), illumination wavelength, scattering particle size, a, refractive index mismatch between the particles the background media, $n_r = n_2/n_1$, where $n_2$ is the refractive index of scattering particles and $n_1$ is the refractive index of the background.

The polarization states of the incident and the scattered electric fields are often described by the Stokes vector, [I Q U V]. The elements of the stokes vector are related to the parallel and perpendicular polarized components of the electric field as:

$$I = \langle |E_\||^2 + |E_\perp|^2 \rangle \quad (3A)$$

$$Q = \langle |E_\||^2 - |E_\perp|^2 \rangle \quad (3B)$$

$$U = \langle E_\| E^*_\perp + E_\perp E^*_\| \rangle \quad (3C)$$

$$V = \langle E_\| E^*_\perp - E_\perp E^*_\| \rangle \quad (3D)$$

Moreover, the relation between the incident and scattered fields stokes vectors is given by:

$$\begin{bmatrix} I_S \\ Q_S \\ U_S \\ V_S \end{bmatrix} = \frac{1}{k^2 R^2} M \begin{bmatrix} I_i \\ Q_i \\ U_i \\ V_i \end{bmatrix} = \frac{1}{k^2 R^2} \begin{bmatrix} S_{11} & S_{12} & 0 & 0 \\ S_{12} & S_{22} & 0 & 0 \\ 0 & 0 & S_{33} & S_{34} \\ 0 & 0 & -S_{34} & S_{33} \end{bmatrix} \begin{bmatrix} I_i \\ Q_i \\ U_i \\ V_i \end{bmatrix} \quad (4)$$

In Eq. (4), M is the Muller matrix. The elements of the Muller matrix are related to $S_1(\theta)$ and $S_2(\theta)$ as:

$$S_{11} = 1/2(|S_2|^2 + |S_1|^2) \quad (5A)$$

$$S_{12} = 1/2(|S_2|^2 - |S_1|^2) \quad (5B)$$

$$S_{33} = 1/2(S^*_2 S_1 + S_2 S^*_1) \quad (5C)$$

$$S_{34} = 1/2i(S_1 S^*_2 - S_2 S^*_1) \quad (5C)$$

The Stokes formulation is enabling to superimpose the Stokes parameters of the light scattered by a collection of randomly separated particles.

The polarized MCRT algorithm of Ramella-Roman et al. was used to simulate the polarized diffuse remittance flux profile. FIG. 15B presents a diagram of the ray tracing process. The polarized MCRT is similar to the conventional MCRT in that it tracks the path of a large number of photons from the illumination source to the detection plane to get the statistically accurate estimate of the received photon flux. Accordingly, the trajectory of a photon is simulated as a random walk in the 3-dimensional space. Upon each photon-particle collision, the traveling direction of the photon is altered. In a conventional MCRT algorithm, the azimuth and polar angle of scattering are randomly generated using marginal probability function distributions of the two angles by exploiting for example a uniform random number generated and a second random number generator based on the scattering phase function. In contrast, in a polarized MCRT algorithm, the polar and azimuth angle of scattering are randomly generated using a joint probability distribution function by exploiting for example the "rejection method". The rejection method is implemented, for example, with the use of a software random number generator, by simultaneously assigning random numbers to the polar and azimuth angles of scattering, based on the joint probability distribution function.

The distance between successive scattering and absorption events are assigned based on the scattering and absorption coefficients ($\mu_s$ and $\mu_a$), using additional random number generators.

An embodiment of the polarized MCRT algorithm according to the invention (FIG. 15B) was employed to simulate the polarized diffuse remittance patterns and to derive the Î versus a calibration curves for various refractive index pairs and illumination wavelengths. The Polarized MCRT model incorporated all experimental LSR parameters, and a focused Gaussian beam was assumed to illuminate the sample placed in a spectroscopic cuvette/imaging chamber (10 mm light path, 1.5 ml volume). A total of one million photons were tracked from the source 110 to the optical detector 132. Various illumination and detection wavelengths and polarization states were considered. The embodiment of the polarized MCRT algorithm incorporated attributes of the polarization state by tracking the Stokes' vector, [I Q U V], with respect to the corresponding reference frame. Meridian plane equations were used to modify the Stokes' vector upon scattering and transport within the medium. In other words, upon each photon-particle interaction or scattering, the Stokes vector was updated via multiplication to the Mueller matrix as shown above. (Alternatively, "Euler" or "Quaternion" MCRT formalisms may be used to simulate the remitted polarized flux patterns). At the detector site, a final rotation was applied (with the detection polarizer) to redefine the Stokes' vector in the receiver coordinates system and the rapidly evolving speckle pattern of the polarized component, exhibiting assorted angles, such as for example parallel, perpendicular, 45°, and/or rotating with respect to the incident polarization state were calculated.

The elements of the Mueller matrix depend on scattering particle size, refractive index mismatch, and illumination wavelength.

The polarized MCRT algorithm was employed to address the situation of poly-dispersity, as explained above. The results of FIG. 13 are obtained using this modified polarized MCRT code. More specifically, the use of the Stokes formulation enables one to superimpose the Stokes parameters of the light scattered by a collection of randomly separated particles. Thus, the Mie scattering solution corresponding to poly-dispersed materials was obtained by averaging the $S_1(\theta)$ and $S_2(\theta)$ over the scattering particle size distribution. Subsequently, Mueller matrix elements were derived from the averaged $S_1(\theta)$ and $S_2(\theta)$.

In conclusion, what was investigated was a particle-sizing scheme based on azimuth-angle dependence of a DRP; the scheme may be conveniently integrated into the LSR system. The information on particle size dimensions is necessary in order to accurately quantify $G^*(\omega)$ of materials using LSR. Such quantification may be performed with or without compensation for multiple scattering and/or absorption in laser speckle rheology as disclosed in PCT/US2013/059906.

In accordance with examples of embodiments disclosed above, proposed is the methodology of determination of a size of light-scatterers in a sample from laser speckle images that accounts for refractive index mismatch between the light scatterers and the surrounding medium of the sample, so that the viscoelastic modulus of the sample may be calculated via laser speckle rheology (LSR). The incorporation of the influence of the index mismatch on the particle sizing process has not been addressed by related art so far. Accordingly, disclosed is a method for determining viscoelastic modulus of a sample from laser speckle patterns, which includes a step of detecting (with an optical detector of the LSR imaging system) light that has interacted with the sample to form an image of laser speckle associated with scattering of the light at light-scattering particles of the sample (which light scattering particles are particles inherent to the sample). In one implementation, the sample is free of external influence such as pressure or external force applied for particle activation and, in addition or alternatively, the sample may be moving or stationary (and, in particular, it may contain an in-vivo non-circulating biofluid or biofluid component). The step of detecting may include detecting light in a sequence of images of the laser speckle to determine changes of the viscoelastic modulus with time. The method further includes a process of forming a spatial pattern of the DRP as a function of angle (for example, an azimuth angle in a plane of the optical detector) representing the laser speckle image (optionally, as a result of time-averaging approach), and determining, from the formed DRP pattern, an experimental value of a ratio of a first normalized irradiance to a second normalized irradiance. The first normalized irradiance may be a value of irradiance of light, from the DRP pattern, that corresponds to a first value of the angle, while the second normalized irradiance being a value of irradiance of light, from said DRP pattern, corresponding to a second value of the angle. (The first and second values of the angle may be chosen such as to maximize a change of the resulting experimental ratio per unit of a change in size of the light scattering particles, for example). The method may further include defining an average size of the light-scattering particles of the sample based on locating a point that corresponds to the experimental value of the ratio, on a reference, pre-determined map representing dependencies of values of said ratio on average size values for different values of index mismatch parameter. The index mismatch parameter is defined to differentiate the index of the material of light-scattering particles from the index of the material of the sample medium in which such particles are contained. In one case, the index mismatch parameter may be defined by a ratio of the corresponding indices of refraction, but generally a differently defined index mismatch parameter can be used (such as a refractive index difference, for example). According to an embodiment of the invention, the calculation of the viscoelastic modulus of the sample now takes into account and incorporates the so-determined average size of light-scattering particles, and may additionally include the use of autocorrelation curve(s) determined from the LSR image(s) of the laser speckle pattern and the mean-square displacement of the light-scattering particles calculated from these autocorrelation curves. Thus, using the same optical instrument to acquire laser speckle images, one can calculate the scattering particle size (from time-averaged speckle images) and the viscoelastic modulus (from time-resolved speckle images). When the sample contains blood or blood components, the method may additionally include a step of deriving from the optical data representing LSR image(s), and with a programmed processor operably cooperated with the LSR imaging system, parameters of a blood coagulation cascade including clotting time (CT) and at least one of total coagulation time, clot formation time (CFT), maximum clot firmness (MCF), maximum lysis (ML), percentage of lost clot stability at a selected point in time, rate of clotting, fibrinolysis time, clot compliance, and clot viscosity.

It is appreciated that the measurement of the DRP from the total flux of light reaching the optical detector may amount to either measuring a summation of speckle patterns varying in time or measurements of diffused light that is substantially incoherent.

In accordance with the examples of the embodiments, a system for use in determining a viscoelastic modulus of a sample was proposed. Such system includes an optical illumination portion configured to deliver light to the sample; a data acquisition portion with an optical detector unit that is configured to receive light (delivered to the sample by the optical illumination portion and that has interacted with the sample) to acquire optical data representing scattering of said light by multiple light-scattering events within the sample; and a processor operably cooperated with said optical data acquisition portion. The processor is specifically programmed to determine a size of the light-scattering particles causing the multiple light-scattering events based on a diffuse remittance profile (DRP) derived from the optical data; and to calculate a mean square displacement (MSD) value for said light-scattering particles and a mechanical property of the sample from the optical data. In a particular implementation, the optical illumination portion includes a first optical polarizer unit; the optical data acquisition portion includes a second optical polarizer unit, and t least one of the first and second optical polarizer units define respectively corresponding first and second polarization states of light transmitted therethrough in a variable fashion. The first and second optical polarizer units disposed in optical communication such that light that has passed through the first unit interacts with the sample and then passes through the second unit towards the optical detector unit. Specifically, at least one of the first and second optical polarizer units may be configured to vary a polarization state of light propagating therethrough in response to an input applied to the at least one of the first and second optical polarizer units (for example, at least one of the first and second optical polarizer units may include at least one of an electro-optical material, a photo-elastic material, and a liquid-crystal material the properties of which are modulated, in real time, by the user). The first and second states of polarization of light transmitted through the first and second polarizer units may be equal. For example the first and second states of polarization include linear polarizations may have corresponding vectors that are collinear, as viewed along a direction of propagation of light through the first and second optical polarizer units. Alternatively, these vectors may be transverse to one another. The system may be structured such that a first optical axis of the optical illumination portion forms a first angle with respect to a surface of the sample, and a second optical axis defined by the optical data acquisition portion forms a second angle with respect to the surface, the first and second angles being different. The optical illumination portion may include at least one light source configured to generate light at at least one wavelength: it may include a wavelength-tunable laser source; a source of incoherent light, a broadband source of light.

While specific values chosen for this embodiment are recited, it is to be understood that, within the scope of the invention, the values of all of parameters may vary over wide ranges to suit different applications.

The disclosure of each of patent documents and/or scientific publications referred to in this application is incorporated herein by reference.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole.

Data acquisition and data processing steps facilitating the operability of an embodiment of the invention may be performed by a processor controlled by instructions stored in a memory. The memory may be random access memory (RAM), read-only memory (ROM), flash memory or any other non-transitory tangible storage memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. For example, because the measurements of the light-scattering particle size is rooted in the measurement of a DRP, the particle size can be determined with the use of diffused light as well; light irradiating the sample under test may be generated by a laser source (at a single wavelength or at multiple wavelengths), by a broadband source, or a source of incoherent electromagnetic radiation. The use of the laser source and laser speckle in this disclosure was provided for illustration purposes only. In another example, as part of analysis of the DPR pattern a shape metric of said pattern may be determined with a programmable processor. Such metric may include at least one of a shape of a pattern lobe, a pattern lobe width, an angle between lobes of the pattern, a number of pattern lobes, and a separation of a lobe peak from a center of said pattern.

Disclosed aspects, or portions of these aspects, may be combined in ways not listed above. Accordingly, the invention should not be viewed as being limited to the disclosed embodiment(s).

The invention claimed is:

1. A system for use in determining a viscoelastic modulus of a sample, the system comprising:
   an optical illumination portion comprising at least one light source configured to deliver light to the sample;
   an optical data acquisition portion including an optical detector configured to receive light, that has been delivered to the sample by the optical illumination portion and that has interacted with the sample, to acquire optical data representing scattering of said light by multiple light-scattering events within the sample; and
   a processor operably cooperated with said optical data acquisition portion and programmed to:
      determine a diffuse remittance profile (DRP) derived from the optical data,
      determine a pattern of the DRP as a function of angle in a plane of an optical detector,
      determine an average size of the light-scattering particles causing the multiple light-scattering events within the sample by comparing a first value with a map of second values,
      the first value defined by a distribution of light irradiance in said pattern, and
      the second values characterizing distributions of light irradiance across radiant flux profiles that have been theoretically calculated as functions of (i) a first variable representing average sizes of light-scattering particles and (ii) a second variable representing refractive index mismatch between the light-scattering particles and a medium containing said particles,
      calculate a mean square displacement (MSD) value for said light-scattering particles and a mechanical property of the sample from the optical data, and
      determine a viscoelastic modulus based on the size of the light-scattering particles and the MSD value for the light-scattering particles.

2. A system according to claim 1, wherein the optical illumination portion includes a first optical polarizer unit; wherein the optical data acquisition portion includes a second optical polarizer unit, at least one of the first and second optical polarizer units variably defining respectively corresponding first and second polarization states of light transmitted therethrough, the first and second optical polarizer units disposed in optical communication such that light that has passed through the first optical polarizer unit interacts with the sample and then passes through the second optical polarizer unit towards the optical detector unit.

3. A system according to claim 2, wherein at least one of the first and second optical polarizer units is configured to vary a polarization state of light propagating therethrough in response to an input applied to the at least one of the first and second optical polarizer units.

4. A system according to claim 3, wherein the at least one of the first and second optical polarizer units includes at least one of an electro-optical material, a photo-elastic material, and a liquid-crystal material.

5. A system according to claim 2, wherein the first optical polarizer unit defines a first state of polarization of light transmitted therethrough towards the sample, the second optical polarizer unit defines a second state of polarization of light transmitted therethrough towards the optical detector, the first and second states of polarization being equal.

6. A system according to claim 5, wherein the first and second states of polarization include linear polarizations having corresponding vectors that are collinear, as viewed along a direction of propagation of light through the first and second optical polarizer units.

7. A system according to claim 5, wherein the first and second states of polarization include linear polarizations having corresponding vectors that are transverse to one another, as viewed along a direction of propagation of light through the first and second optical polarizer units.

8. A system according to claim 1, wherein a first optical axis of the optical illumination portion forms a first angle with respect to a surface of the sample, and a second optical axis defined by the optical data acquisition portion forms a second angle with respect to the surface, the first and second angles being different.

9. A system according to claim 1, wherein the optical illumination portion includes at least one light source is configured to generate light at at least one wavelength.

10. A system according to claim 9, wherein the at least one light source includes a wavelength-tunable laser source.

11. A system according to claim 9, wherein the at least one light source includes a source of incoherent light.

12. A system according to claim 9, wherein the at least one light source includes a broadband source of light.

13. A system according to claim 1, wherein the optical illumination portion is configured to irradiate sample with light at multiple wavelengths, and wherein the DRP and the radiant flux profiles have been determined as functions of (iii) a third variable representing a wavelength of said light.

14. A system according to claim 13, further comprising a tangible, non-transitory storage medium containing reference data representing said map of second values as a function of at least one of the first, second, and third variables.

15. A system according to claim 1, wherein the first value is defined by first and second normalized irradiances determined, respectively, at first and second angles from said pattern.

16. A system according to claim 15, wherein the first value is a ratio of said first and second normalized irradiances.

17. A system according to claim 1, wherein the processor is further programmed to define a shape metric of said pattern, said shape metric including at least one of a shape of a pattern lobe, a pattern lobe width, an angle between lobes of the pattern, a number of pattern lobes, and a separation of a lobe peak from a center of said pattern.

18. A system according to claim 1, wherein the processor is further programmed to calculate a value of the viscoelastic modulus of said sample from data that represents mean square displacements of the light-scattering particles of the sample.

19. A system according to claim 1, wherein the processor is further programmed to derive from the optical data, when the sample includes blood, parameters of a blood coagulation cascade that include clotting time (CT) and at least one of total coagulation time, clot formation time (CFT), maximum clot firmness (MCF), maximum lysis (ML), percentage of lost clot stability at a selected point in time, rate of clotting, fibrinolysis time, clot compliance, and clot viscosity.

20. A system according to claim 1, wherein the processor is further programmed to calculate at least one of an absorption coefficient and a reduced scattering coefficient of the sample based at least on the DRP determined from the optical data that have been averaged over time.

21. A method for determining a viscoelastic modulus of a sample with the use of an optical system, the method comprising:
   acquiring, with an optical detector, optical data representing time evolution of a speckle associated with light-scattering particles of the sample irradiated with light from a light source;
   determining an average size of said light-scattering particles based on an angle-dependent pattern of a diffuse remittance profile (DRP) derived from acquired optical data;
   calculating, with a programmable processor, a value of mean square displacement (MSD) of the light-scattering particles and a mechanical property of the sample from the acquired optical data, said MSD being a function of said size; and
   estimating, with the programmable processor and from said angle-dependent pattern, an experimentally-determined value of a ratio of a first normalized irradiance to a second normalized irradiance, the first and second normalized irradiances being defined by said angle-dependent pattern at first and second values of an angle, respectively.

22. A method according to claim 21, further comprising determining an optical property of the sample based, in part, on the radiant flux profile determined from acquired optical data.

23. A method according to claim 22, wherein determining an optical property includes calculating at least one of an absorption coefficient and a reduced scattering coefficient of the sample based at least on the radiant flux profile determined from the optical data that have been averaged over time.

24. A method according to claim 21, further comprising determining a frequency-dependent value of viscoelastic modulus characterizing the sample based on said size and said MSD.

25. A method according to claim 21, wherein said acquiring includes detecting light from a irradiance distribution formed at the optical detector by said light, that has interacted with the sample, by varying at least one of i) polarization state and ii) wavelength of said light, and said determining includes determining an averaged size of light-scattering particles of the sample.

26. A method according to claim 21, further comprising defining an average size of said light-scattering particles based on comparison of the experimentally-determined value of ratio with a reference map, the reference map representing dependencies of values of said ratio theoretically-calculated as a function of average sizes for different values of a refractive index mismatch between a material of light-scattering particles and a material of the sample's medium in which said light-scattering particles are contained.

27. A method according to claim 26, wherein said reference map represents dependencies of values of said ratio theoretically-calculated as a function of average sizes, said values of the refractive index mismatch, and optical wavelengths.

28. A method according to claim 21, further comprising defining the first and second angles to maximize a change of the experimental value of a ratio per unit of a change in size of light-scattering particles.

29. A method according to claim 21, wherein said acquiring includes detecting light in a sequence of images of the speckle, and further comprising calculating a value of the viscoelastic modulus from data that represents frequency-dependent MSD of said light-scattering particles and that is determined with the use of autocorrelation analysis from a sequence of speckle images, wherein said calculating includes accounting for said size.

30. A method according to claim 21, wherein said acquiring includes detecting light from a laser speckle formed by light-scattering particles of a sample containing blood, and further comprising deriving from said optical data, with a programmed processor operably cooperated with said optical data acquisition system, parameters of a blood coagulation cascade, said parameters including clotting time (CT) and at least one of total coagulation time, clot formation time (CFT), maximum clot firmness (MCF), maximum lysis (ML), percentage of lost clot stability at a selected point in time, rate of clotting, fibrinolysis time, clot compliance, and clot viscosity.

31. A method according to claim 21, further comprising varying at least one of a wavelength of light delivered to the sample and a polarization state of light propagating through the optical system.

32. A method according to claim 31, wherein said varying includes changing an operational status of at least one of i) a polarizer of an illumination portion of the optical system and ii) an analyzer of the optical detection portion of the optical system.

33. A method according to claim 21, further comprising calculating at least one of an absorption coefficient and a reduced scattering coefficient of the sample based at least on the DRP determined from the optical data that have been averaged over time.

34. A system for use in determining a viscoelastic modulus of a sample, the system comprising:
   an optical illumination portion comprising a light source configured to deliver light to the sample;
   an optical data acquisition portion including an optical detector to receive light that has been delivered to the sample by the optical illumination portion and that has interacted with the sample, and to acquire optical data representing scattering of said light by multiple light-scattering events within the sample; and
   a processor operably cooperated with said optical data acquisition portion and programmed to:
      determine an average size of said light-scattering particles causing the multiple light-scattering events based on an angle-dependent pattern of a diffuse remittance profile (DRP) based on the optical data,
      calculate a mean square displacement (MSD) value for said light-scattering particles and a mechanical property of the sample from the optical data, the MSD being a function of the size, and
      estimate, from the angle-dependent pattern, an experimentally-determined value of a ratio of a first normalized irradiance to a second normalized irradiance, the first and second normalized irradiances being defined by said angle-dependent pattern at first and second values of an angle, respectively.

\* \* \* \* \*

UNITED STATES PATENT AND TRADEMARK OFFICE
CERTIFICATE OF CORRECTION

PATENT NO. : 10,191,031 B2
APPLICATION NO. : 15/114868
DATED : January 29, 2019
INVENTOR(S) : Seemantinin K. Nadkarmi et al.

It is certified that error appears in the above-identified patent and that said Letters Patent is hereby corrected as shown below:

In the Specification

Column 2, Line 54, "a, of" should be --$\alpha$, of--.

Column 3, Line 3, "a, obtained" should be --$\alpha$, obtained--.

Column 3, Line 5, "on a" should be --on $\alpha$--.

Column 3, Line 49, "a=3" should be --$\alpha$=3--.

Column 4, Line 43, "a=3" should be --$\alpha$=3--.

Column 4, Line 51, "$\sigma_\alpha/\mu_\alpha$; where $\mu_\alpha$ and $\sigma_\alpha$" should be --$\sigma_a/\mu_a$; where $\mu_a$ and $\sigma_a$--.

Column 5, Line 57, "a(t)=$\partial$" should be --$\alpha$(t)=$\partial$--.

Column 7, Line 7, "a and/or" should be --$\alpha$ and/or--.

Column 7, Line 18, "a, and" should be --$\alpha$, and--.

Column 7, Line 20, "$n_i$:" should be --$n_1$:--.

Column 8, Line 51, "a and" should be --$\alpha$ and--.

Column 9, Line 32, "a=(100" should be --$\alpha$=(100--.

Column 9, Line 43, "a=0.1" should be --$\alpha$=0.1--.

Column 9, Line 50, "of a)" should be --of $\alpha$)--.

Signed and Sealed this
Twenty-sixth Day of March, 2019

Andrei Iancu
*Director of the United States Patent and Trademark Office*

CERTIFICATE OF CORRECTION (continued)
U.S. Pat. No. 10,191,031 B2

Column 9, Line 51, "of a)" should be --of $\alpha$)--.

Column 9, Line 52, "of a is" should be --of $\alpha$ is--.

Column 10, Line 7, "size a" should be --size $\alpha$--.

Column 10, Line 12, "vs. a" should be --vs. $\alpha$--.

Column 10, Line 17, "a=0.1" should be --$\alpha$=0.1--.

Column 10, Line 21, "a, $\hat{I}$" should be --$\alpha$, $\hat{I}$--.

Column 10, Line 23, "a from" should be --$\alpha$ from--.

Column 10, Line 30, "a value" should be --$\alpha$ value--.

Column 10, Line 41, "a and" should be --$\alpha$ and--.

Column 10, Line 44, "a for" should be --$\alpha$ for--.

Column 12, Line 17, "$a_1$" should be --$\alpha_1$--.

Column 12, Line 17, "$a_2$" should be --$\alpha_2$--.

Column 14, Line 63, "a, and" should be --$\alpha$, and--.

Column 15, Line 35, "a=3" should be --$\alpha$=3--.

Column 15, Line 49, "a/$\lambda$" should be --$\alpha$/$\lambda$--.

Column 15, Line 53, "a=3" should be --$\alpha$=3--.

Column 15, Line 56, "a=3" should be --$\alpha$=3--.

Column 16, Line 7, "a value" should be --$\alpha$ value--.

Column 16, Line 17, "(a=100" should be --($\alpha$=100--.

Column 16, Line 25, "a/$\lambda$" should be --$\alpha$/$\lambda$--.

Column 16, Line 29, "a, calculated" should be --$\alpha$, calculated--.

Column 18, Line 15, "$\sigma_\alpha/\mu_\alpha$; where $\mu_\alpha$ and $\sigma_\alpha$" should be --$\sigma_a/\mu_a$; where $\mu_a$ and $\sigma_a$--.

Column 18, Line 21, "a, and" should be --$\alpha$, and--.

CERTIFICATE OF CORRECTION (continued)
U.S. Pat. No. 10,191,031 B2

Column 18, Line 22, "a and" should be --$\alpha$ and--.

Column 18, Line 64, "$\mu_\alpha=3$" should be --$\mu_a=3$--.

Column 18, Line 64, "$\sigma_\alpha$" should be --$\sigma_a$--.

Column 19, Line 37, "a, refractive" should be --$\alpha$, refractive--.